US007074915B2

(12) United States Patent
Soreq et al.

(10) Patent No.: US 7,074,915 B2
(45) Date of Patent: Jul. 11, 2006

(54) ANTISENSE OLIGONUCLEOTIDE AGAINST HUMAN ACETYLCHOLINESTERASE (ACHE) AND USES THEREOF

(75) Inventors: Hermona Soreq, Jerusalem (IL); Shlomo Saidman, deceased, late of Gush Etzion (IL); by Jackiline Saidman, legal representative, Gush Etzion (IL); Tama Evron, Mevasseret Zion (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 187 days.

(21) Appl. No.: 10/402,016

(22) Filed: Mar. 27, 2003

(65) Prior Publication Data

US 2003/0216344 A1    Nov. 20, 2003

Related U.S. Application Data

(63) Continuation-in-part of application No. PCT/IL02/00411, filed on May 23, 2002.

(30) Foreign Application Priority Data

May 24, 2001 (IL) ...................................... 143379

(51) Int. Cl.
  *C07H 21/04* (2006.01)
  *A61K 48/00* (2006.01)
(52) U.S. Cl. ........................................ 536/24.5; 514/44
(58) Field of Classification Search ............... 536/24.5; 514/44
  See application file for complete search history.

(56) References Cited

U.S. PATENT DOCUMENTS

| 5,455,044 A | 10/1995 | Kim et al. |
| 5,558,852 A | 9/1996 | Bigner et al. |
| 5,891,725 A * | 4/1999 | Soreq et al. ................. 435/377 |
| 6,110,742 A * | 8/2000 | Soreq et al. ................. 435/375 |

FOREIGN PATENT DOCUMENTS

| WO | WO 9822132 | 5/1998 |
| WO | WO 9826062 | 6/1998 |
| WO | WO 0136627 | 5/2001 |

OTHER PUBLICATIONS

Soreq et al. Antisense oligonucleotide inhibition of acetylcholinesterase gene expression induces progenitor cell expansion and suppresses hematopoietic apoptosis ex vivo. Aug. 1994 Proc. Natl. Acad. Sci. USA, vol., 91. pp. 7907-7911 (esp. 7908).*
Webster's II New Riverside University Dictionary 1994 The Riverside Publishing Company (see p. 1194).*
Abe et al. (1998)*Antivir. Chem. Chemother.* 9, 253-62.
Agrawal S. and Kandimalla E.R. (2000) *Mol. Med. Today*, 6, 72-81.
Bai et al. (1998) Ann *Thorac. Surg.* 66, 814-9.
Ben Nathan D. et al. (1991) *Life .Sci.* 48, 1493-1500.
Berrouschot et al. (1997) *Crit. Care Med.* 25, 1228-35.
Bochot et al. (1998)*Pharm. Res.* 15, 1364-9.
Boneva, N. et al. (2000) *Muscle & Nerve 23*, 1204-8.
Capaccioli et al. (1993)*Biochem. Biophys. Res. Comm.* 197, 818.
Cohen, O. et ;al. (2002) *Mol. Psychiatry* 7, 874-885.
Conaty et al. (1999) *Nucleic Acids Res.* 27, 2004-2407.
Crooke S. T. (2000) *Methods Enzymol.* 313, 3-45.
de Angelis, L.M. (2001) JV. *Engl. JMed.* 344(2), 114-123.
Drachman, D.B. (1994) *N Eng J Med 330*, 1797-810.
Galyam, N. et al. (2000) *Antisense Nucl Acid Drug Dev 11*, 51-57.
Gerster et al. (1998)Anal. *Biochem.* 262, 177-84.
Goldstein and Betz (1986) *Scientific American*, Sep., pp. 70-79.
Grifman, M., and Soreq, H. (1997) *Antisense Nucleic Acid Drug Dev 7*, 351-9.
Grosari D. et al. (2001) *Mol. Med.* 7, 93-105.
Hall and Sanes (1993) *Cell* 72 /Neuron vol. 10 (Suppl.), 99-121.
Haseloff and Gerlach (1998) *Nature* 334, p. 585-591.
ImperatoA. et al. (1991) *Brain Res.* 538, 111-117.
Kanamaru et al. (1998) J. *Drug Target* 5, 235-46.
Kita and Saito (1991)*Int. J. Cancer* 80, 553-8.
Koenigsberger C. et al. (1997) *J. Neurochem.* 69, 1389-1397.
Legay et al. (1993), *J. Neurochem.* 60(1), 337-346.
Lesnik, E.A. & Freier, S.M. (1998) *Biochemistry* 37, 6991-7.
Monia, B. P. (1997) *Ciba Found. Symp. 209*, 107-119.
Nakamura et al.(1998) *Gene Ther.* 5, 1455-61.
Noguchi et al. (1998)*FEBS Lett.* 433, 169-73.
Pere Ruiz (1999) *Antisense Nucleic Acid Drug Dev.*, 9, 33.
Quattrone et al. (1995) *Biochemica* 1, 25.
Rachinsky et al. (1990) *Neuron* 5(3), 317-327.

(Continued)

*Primary Examiner*—Jane Zara
*Assistant Examiner*—Jon B. Ashen
(74) *Attorney, Agent, or Firm*—John P. White, Esq.; Cooper & Dunham LLP

(57) ABSTRACT

The invention relates to an antisense oligonucleotide targeted to the coding region of the human acetylcholinesterase (AChE), which selectively suppresses the AChE-R isoform of the enzyme. The antisense oligonucleotide is intended for use in the treatment and/or prevention of neuromuscular disorders, preferably myasthenia gravis. In addition, it can penetrate the blood-brain barrier (BBB) and destroy AChE-R within central nervous system neurons, while also serving as a carrier to transport molecules across the BBB.

14 Claims, 25 Drawing Sheets

OTHER PUBLICATIONS

Sarver et al. (1990) *Science* 247, p. 1222.
Seidman S. et al. (1999) *Antisense Nucl. Acid Drug Devel*, 9, 333-340.
Sharma H.S. et al. (1992) *Prog. Brain Res.* 91, 189-196.
Shoji et al. (1998) *J. Drug Target* 5, 261-73.
Soni et al. (1998) *Hepatology*, 28, 1402-10.
Soreq, H., and Seidman, S. (2001) *Reviews Neuroscience* 2, 294-302.
Soukchareun et al. (1998) *Bioconjug. Chem.* 9, 466-75.
Sugawa et al. (1998) *J. Neurooncol.* 39, 237-44.
Tavitan et al. (1998) *Nat Med* 4(4): 467-71.
Triggs et al. (1992) *Muscle Nerve* 15, 267-72.
Vincent A. (1999) *Curr. Opin Neurol.* 12, 545-551.
Waelti et al. (1998) *Int. J. Cancer*, 77, 728-33.
Wang, J. (1998) *Controlled Release* 53, 39-48.
Wittbrodt (1994) *Arch. Intern. Med.*, 157, 399-408.
Xu et al. (1999) *Endocrinology*, 140, 2134-44.
Yang et al. (1998) *Circ. Res.* 83, 552-9.
Andres et al., Acetylcholinesterase-transgenic mice display embryonic modulations in spinal cord choline acetyltransferase and neurexin Iβ gene expression followed by late-onset neuromotor deterioration. *Proc. Natl. Acad. Sci. USA.* 94:8173-8178 (1997).
Ben Aziz-Aloya et al., Expression of human acetylcholinesterase promoter-reporter construct in developing neuromuscular junctions of *Xenopus* embryos. *Proc. Natl. Acad. Sci. USA.* 90:2471-2475 (1993).
Ellman et al., A New and Rapid Colorimetric Determination of Acetylcholinesterase Activity. *Biochemical Pharmacology.* 7:88-95 (1961).
Friedman et al., Pyridostigmine brain penetration under stress enhances neuronal excitability and induces early immediate transcriptional response. *Nature Medicine.* 2:1382-1385 (1996).
Kaufer et al., Acute stress facilitates long-lasting changes in cholinergic gene expression. *Nature.* 393:373-377 (1998).
Koenisberger et al., Neurite Differentiation Is Modulated in Neuroblastoma Cells Engineered for Altered Acetylcholinesterase Expression. *J. Neurochem.* 69:1389-1397 (1997).
Lev-Lehman et al., Synaptogenesis and Myopathy Under Acetylcholinesterase Overexpression. *J. Mol. Neurosci.* 14:93-105 (2000).

Meshorer et al., Alternative Splicing and Neuritic mRNA Translocation Under Long-Term Neuronal Hypersensitivity. *Science.* 295:508-512 (2002).
Meyer et al., Cationic Liposomes Coated with Polyethylene Glycol As Carriers for Oligonucleotides. *J. Biol. Chem.* 273(25):15621-15627 (1998).
Ratajczak et al., *In vivo* treatment of human leukemia in a *scid* mouse model with c-myb antisense oligodeoxynucleotides. *Proc. Natl. Acad. Sci. USA.* 89:11823-11827 (1992).
Rossi et al., Localization of "Non-extractable" Acetycholinesterase to the Vertebrate Neuromuscular Junction. *J. Bio. Chem.* 268(25):19152-19159 (1993).
Seidman et al., Overexpressed Monomeric Human Acetylcholinesterase Induces Subtle Ultrastructural Modifications in Developing Neromuscular Junctions of *Xenopus laevis* Embryos, *J. Neurochem.* 62(5):1670-1681 (1994).
Seidman et al:, Synaptic and Epidermal Accumulations of Human Acetylcholinesterase Are Encoded by Alternative 3'-Terminal Exons. *Mol. And Cell. Biol.* 15(6):2993-3002 (1995).
Shapira et al., A transcription-activating polymorphism in the *ACHE* promoter associated with acute sensitivity to ant-acetylcholinesterases. *Human Molecular Genetics.* 9(9):1273-1281 (2000).
Soreq et al., Molecular cloning and construction of the coding region for human acetylcholinesterase reveals a G+C-rich attenuating structure. *Proc. Natl. Acad. Sci. USA.* 87:9688-9692 (1990).
Sternfeld et al., Acetylcholinesterase Enhances Neurite Growth and Synapse Development through Alternative Contributions of Its Hydrolytic Capacity, Core Protein, and Variable C Termini. *J. Neurosci.* 18(4):1240-1249 (1998).
Sternfeld et al., Excess "read-through" acetylcholinesterase attenuates but the "synthetic" variant intensifies neurodeterioration correlates. *Proc. Natl. Acad. Sci. USA.* 97(15)8647-8652 (2000).
Shohami et al., Antisense prevention of neuronal damages following head injury in mice. *J. Mol. Med.* 78:228-236 (2000).

\* cited by examiner

| DEFINITION | Human acetylcholinesterase (ACHE) mRNA, complete cds. |
|---|---|
| ACCESSION | M55040 |
| VERSION | M55040.1 GI:177974 |
| SOURCE | Human 21-week old fetus DNA, and cDNA to mRNA |
| ORGANISM | Homo sapiens |
| AUTHORS | Soreq,H.E., Ben-Aziz,R., Prody,C.A., Seidman,S., Gnatt,A., Neville,L., Lieman-Hurwitz,J., Lev-Lehman,E., Ginzberg,d., Lapidot-Lifson,Y. and Zakut,H. |
| TITLE | Molecular cloning and construction of the coding region for human Acetylcholinesterase reveals a G+C-rich attenuating structure |
| JOURNAL | Proc. Natl. Acad. Sci. U.S.A. 87(24), 9688-9692(1990) |
| MEDLINE | 91088577 |

Human AChE

```
  1 ctctcccctc atctttgcca acctgcccca cctcctctgc agctgc taacccttgg
 61 gccgacagtg ccctaatctc ctccctcctg gctctcgac cgaccctcca ccctttccct
121 ttctttctcc cagcagacgc cgcctgccct gcagccatga ggccccgca gtgtctgctg
181 cacacgcctt ccctggcttc cccactcctt ctcctcctcc tctggctcct gggtggagga
241 gtgggggctg agggccggga ggatgcagag ctgctggtga cggtgcgtgg gggccggctg
301 cggggcattc gcctgaagac ccccggggc cctgtctctg ctttcctggg catcccctt
361 gcggagccac ccatgggacc ccgtcgcttt ctgccaccgg agcccaagca gcctggtca
421 ggggtggtag acgctacaac cttccagagt gtctgctacc aatatgtgga cacctatac
481 ccaggttttg agggcaccga gatgtggaac cccaaccgtg agctgagcga ggactgcctg
541 tacctcaacg tgtggacacc ataccccgg cctacatcc ccacccctgt cctcgtctgg
601 atctatgggg gtggcttcta cagtggggcc tcctcctgg acgtgtacga tggccgcttc
661 ttggtacagg ccgaggac tgtctggtg tccatgaact accgggtggg agcctttggc
721 ttcctggccc tgccggggag ccgagaggcc ccgggcaatg tgggtctcct ggatcagagg
781 ctggccctgc agtgggtgca ggagaacgtg gcagccttcg ggggtgaccc gacatcagtg
841 acgctgtttg gggagagcgc gggagccgcc tcggtgggca tgcacctgct gtccccgccc
``` hAS3
795-5' ggtgcaggagaacgtggcag 3'-814 Coding Sequence
   3' ccacgtcctcttgcaccgtc   5' Complementary Sequence
   5' CTGCCACGTTCTCCTGCACC 3' ASODN Sequence   (SEQ ID NO: 1)=hEN101

Fig. 1 hEN101    5'- CTGCCACGTTCTCCTGCACC-3'

Current Oligo, 20-mer [1]:
Current+ Oligo: no 3'-terminal dimer formation

Current- Oligo: no 3'-terminal dimer formation

Current+ Oligo: the most stable dimer overall: 4 br, -6.9kcal/mol
    5' CTGCCACGTTCTCCTGCACC 3'
                  | | | |
              3' CCACGTCCTCTTGCACCGTC 5'
Hairpin:  G=-0.5kcal/mol, Loop=11nt, Tm=34°
    5' CTGCCACGT-┐
                 T
    3' CCACGTCCTC┘

Fig. 2A

Current Oligo, 20-mer [1]:
Td=70.4° [nearest neighbor method]
Tm=74.4° [%GC method]
Tm=66° [2°*(A+T) + 4°*(G+C) method]
Mr = 6045 [one strand]
Mr = 12.4 k [two strands.]
µg/OD = 45.6 [dsDNA]

| Base | Number and % |
|---|---|
| A | 2 [10.0] |
| C | 10 [50.0] |
| G | 3 [15.0] |
| T | 5 [25.0] |
| A+T | 7 [35.0] |
| G+C | 13 [65.0] |

| DNA Melting Temperature in Various Salt and Formamide Concentrations [°C] | | | |
|---|---|---|---|
| [mM] | xSSC | 0% | 10% | 50% |
| 1 | (0.006) | 24.6 | 18.1 | -7.9 |
| 10 | (0.06) | 41.2 | 34.7 | 8.7 |
| 50 | (0.03) | 52.8 | 46.3 | 20.3 |
| 165 | (1) | 61.4 | 54.9 | 28.9 |
| 330 | (2) | 66.4 | 59.9 | 33.9 |
| 500 | (3) | 69.4 | 62.9 | 36.9 |
| 1000 | (6) | 74.4 | 67.9 | 41.9 |

Tm [°C] = 81.5 + 16.6*log[Na] + 0.41*(%GC)-675/length-0.65*(%formamide) – (% mismatch)
Approximate Tm of the mismatched oligo:
(1) 64.4°; (2) 58.4; (3) 52.4°; (4) 45.4°
Mism. Tm = Td – 1.2° x [% mismatch]

Fig. 2B

DEFINITION    Mouse mRNA for acetylcholinesterase.
ACCESSION     X56518
VERSION       X56518.1 GI:49844
SOURCE        house mouse.
ORGANISM      Mus musculus
REFERENCE     1 (bases 1 to 2089)
AUTHORS       Taylor,P.
JOURNAL       Submitted(30-OCT-1990) Taylor P., University of California, San Diego,
              Departament of Pharmacology, La Jolla, CA 92093-0636
REFERENCE     2 (bases 1 to 2089)
AUTHORS       Rachinsky,T.L., Camp,S., Li,Y., Ekstrom,T.J., Newton,M. and Taylor,P.
              Molecular cloning of mouse acetylcholinesterase: tissue
              Distribution of alternatively spliced mRNA species
JOURNAL       Neurpn 5(3), 317-327(1990)
MEDLINE       90380429
Mouse AChE(bases 1-720 shown)

```
  1 atgaggcctc cctggtatcc cctgcataca ccttccctgg cttttccact cccttcctc
 61 ctcctctccc tcctgggagg aggggcaagg gctgaggcc gggaagaccc gcagctgctg
121 gtgagggttc gagggcca gctgaggggc atccgcctga aggcccctgg atttatgcca
181 cacacgcctt ccctggcttc cccactcctt ctcctcctcc tctggctcct gggtggagga
241 ccagagccca agcggccctg gtcaggagtg ttgatgcta ccaccttcca aaatgtctgc
301 cggggcattc gcctgaagac ccccggggggc cctgtctctg cttcctggg catcccctttt
361 cgagagttga gtgaagactg cctgtatctt aatgtgtgga caccataccc cagacctgct
421 tctcccacac cttccctcat ctggatctat gggggtggtt tchacagcgg agcggcctcc
481 ttggatgtgt atgacggccg tttcctggcc caggttgagg gagctgtgtt ggtatctatg
541 aactaccgag tgggaaccct tggcttcttg gccctaccag gaagcagaga agccctggc
601 aatgtaggtc tgctggatca cggcttcc ttgcaatggg tgcaagaaaa tattgcagcc
661 tttgggggcg acccgatgtc agtgactctg tttggggaga gtgcgggtgc agcctccgtg
``` mAS3
639-5'   ggtgcaagaaaatattgcag 3'-658 Coding Sequence
      3' caacgttctttataacgtc 5'    Complementary Sequence
      5' CTGCAATATTTTCTTGCACC 3'   Antisense ODN   (SEQ ID NO: 3) = mEN101

Fig. 3 mEN101  5'- CTGCAATATTTTCTTGCACC-3'

Current Oligo, 20-mer [1]:
Current+ Oligo: no 3'-terminal dimer formation

Current- Oligo: no 3'-terminal dimer formation

Current+ Oligo: the most stable dimer overall: 5 bp, -8.8kcal/mol
    5' CTGCAATATTTTCTTGCACC 3'
       | | | | | | |     | | | | |
    3' CCACGTTCTTTTATAACGTC 5'
Hairpin: G=-4.7 kcal/mol, Loop=7nt, Tm=77°
    5' CTGCAATAT-|
                   T
    3' CCACGTTCTT-|

Fig. 4A

Current Oligo, 20-mer [1]:
Td=60.4° [nearest neighbor method]
Tm=64.2° [%GC method]
Tm=66° [2°*(A+T) + 4°*(G+C) method]
Mr = 6098 [one strand]
Mr = 12.4 k [two strands.]
µg/OD = 48.1 [dsDNA]

| Base | Number and % |
|------|--------------|
| A | 4 [20.0] |
| C | 6 [30.0] |
| G | 2 [10.0] |
| T | 8 [40.0] |
| A+T | 12 [60.0] |
| G+C | 8 [40.0] |

| DNA Melting Temperature in Various Salt and Formamide Concentrations [°C] | | | | |
|------|------|------|------|------|
| [mM] | xSSC | 0% | 10% | 50% |
| 1 | (0.006) | 14.4 | 7.9 | -18.1 |
| 10 | (0.06) | 31.0 | 24.5 | -1.5 |
| 50 | (0.03) | 42.6 | 36.1 | 10.1 |
| 165 | (1) | 51.2 | 44.7 | 38.7 |
| 330 | (2) | 56.2 | 49.7 | 23.7 |
| 500 | (3) | 59.2 | 52.7 | 26.7 |
| 1000 | (6) | 64.2 | 57.7 | 31.7 |

Tm [°C] = 81.5 + 16.6*log[Na] + 0.41*(%GC) - 675/length - 0.65*(%formamide) − (% mismatch)
Approximate Tm of the mismatched oligo:
(1) 54.4°; (2) 48.4; (3) 42.4°; (4) 36.4°
Mism. Tm = Td − 1.2° x [% mismatch]

Fig. 4B

DEFINITION    acetylcholinesterase T subunit (rats, mRNA Partial, 2066 nt).
ACCESSION     S50879
VERSION       S50879.1 GI:262092
SOURCE        Rattus sp.
ORGANISM      Rattus sp.
REFERENCE     1 (bases 1 to 2066)
AUTHORS       Legay,C., Bon,S., Vernier,P., Coussen,F. and Massoulie,J.
TITLE         Cloning and expression of a rat acetylcholinesterase subunit:
              generation of multiple molecular forms and complementarity with a
              Torpedo collagenic subunit
JOURNAL       J. Neurochem. 60(1), 337-346(1993)
MEDLINE       93107932

Rat AChE (bases 1-720 shown)
    1 atgaggcctc cctggtatcc cctgcataca ccctccctgg cttctccact cctcttcctc
   61 ctcctctccc tcctgggagg aggggcaagg gctgagggcc gggaagaccc tcagctgctg
  121 gtgagggttc gaggggggcca gctgaggggc atccgcctga aggcccctgg aggcccagtc
  181 tcagctttc tgggcatccc ctttgcagag ccacctgtgg gctcacgtag atttatgcca
  241 ccagagcca agcgcccctg gtcaggaata ttggatgcta ccaccttcca aaatgtctgc
  301 taccaatacg tggacaccct gtaccctggg tttgagggta ccgagatgtg gaacccccaat
  361 cgagagctga gtgaagactg ccttatctt aatgtgtgga caccataccc caggcctact
  421 tctcccacac ctgtcctcat ctggatctat gggggtggtt tctacagtgg agcatcctcc
  481 ttggacgtgt atgacggccg ttcctggcc caggttgagg gaaccgtgtt ggtatctatg
  541 aactaccgag tgggaacctt tggcttcttg gctctaccag gaagcagaga agccccgc
  601 aatgtaggcc tgctggatca acggcttgcc ttgcaatggg tacaagaaaa tatcgcagcc
  661 tttggggggag acccaatgtc agtgactctg tttggggaga gtgcaggtgc agcctcagtg rAS1
51-5' cctcttcctcctcctctccc        3'-70     Coding Sequence
      3' ggagaaggaggaggagaggg    5'        Complementary Sequence
      5' GGGAGAGGAGGAGGAGAGG 3'            Antisense ODN    (SEQ ID NO: 5) =rEN 102 rAS3
639-5' ggtacaagaaaatatcgcag     3'-658    Coding Sequence
       3' ccatgttctttatagcgtc   5'        Complementary Sequence
       5' CTGCGATATTTTCTTGTACC 3'         Antisense ODN    (SEQ ID NO: 4) =rEN 101

NOTE: AS1 for mouse and rat AChE are identical

Fig. 5 rEN101 5'- CTGCGATATTTTCTTGTACC-3'

Current Oligo, 20-mer [1]:
Current+ Oligo: no 3'-terminal dimer formation

Current- Oligo: no 3'-terminal dimer formation

Current+ Oligo: the most stable dimer overall: 4 bp, -4.0kcal/mol
  5' CTGCGATATTTTCTTGTACC 3'
                | | | |
  3' CCATGTTCTTTTATAGCGTC  5'
No hairpin stems ⊔3 bp

Fig. 6A

Current Oligo, 20-mer [1]:
Td=57.1° [nearest neighbor method]
Tm=64.2° [%GC method]
Tm=56° [2°*(A+T) + 4°*(G+C) method]
Mr  =  6129 [one strand]
Mr  =  12.4 k [two strands.]
µg/OD = 48.1 [dsDNA]

| Base | Number and % |
|---|---|
| A | 3 [15.0] |
| C | 5 [25.0] |
| G | 3 [15.0] |
| T | 9 [45.0] |
| A+T | 12 [60.0] |
| G+C | 8 [40.0] |

| DNA Melting Temperature in Various Salt and Formamide Concentrations [°C] | | | | |
|---|---|---|---|---|
| [mM] | xSSC | 0% | 10% | 50% |
| 1 | (0.006) | 14.4 | 7.9 | -18.1 |
| 10 | (0.06) | 31.0 | 24.5 | -1.5 |
| 50 | (0.03) | 42.6 | 36.1 | 10.1 |
| 165 | (1) | 51.2 | 44.7 | 38.7 |
| 330 | (2) | 56.2 | 49.7 | 23.7 |
| 500 | (3) | 59.2 | 52.7 | 26.7 |
| 1000 | (6) | 64.2 | 57.7 | 31.7 |

Tm [°C] = 81.5 + 16.6*log[Na] + 0.41*(%GC)- 675/length-0.65*(%formamide) − (% mismatch)
Approximate Tm of the mismatched oligo:
(1) 51.1°; (2) 45.1; (3) 39.1°; (4) 33.1°
Mism. Tm = Td − 1.2° x [% mismatch]

Fig. 6B

ANTISENSE OLIGONUCLEOTIDE AGAINST HUMAN ACETYLCHOLINESTERASE (ACHE) AND USES THEREOF

This application is a continuation-in-part of PCT/IL02/00411, filed May 23, 2002, which claims priority of Israeli Application No. 143379, filed May 24, 2001, the contents of which are hereby incorporated by reference into this application.

STATEMENT AS TO FEDERALLY SPONSORED RESEARCH

This work was supported by the US Army Medical Research and Material Command DAMD 17-99-9547 (July 1999–August 2004). Accordingly, the United States Government has certain rights in this invention.

FIELD OF THE INVENTION

The present invention relates to a synthetic antisense oligodeoxynucleotide targeted to the common coding domain of human acetylcholinesterase (AChE) mRNA, and to pharmaceutical or medical compositions comprising the same, particularly for the treatment and/or prevention of a progressive neuromuscular disorder.

BACKGROUND OF THE INVENTION

All publications mentioned throughout this application are fully incorporated herein by reference, including all references cited therein.

Neuromuscular junctions (NMJ) are highly specialized, morphologically distinct, and well-characterized cholinergic synapses [Hall and Sanes (1993) Cell 72 Suppl., 99–121]. Chronic impairments in NMJ activity induce neuromuscular disorders characterized by progressive deterioration of muscle structure and function. The molecular and cellular mechanisms leading from compromised NMJ activity to muscle wasting have not been elucidated.

One such disorder is myasthenia gravis (MG), caused by a defect in neuromuscular transmission mediated by autoantibodies that severely reduce the number of functional post-synaptic muscle nicotinic acetylcholine receptors (nAChR) [Drachman D. G. (1994) N. Engl. J. Med. 330, 1797–1810; Vincent A. (1999) Curr. Opin. Neurol. 12, 545–551]. MG is characterized by fluctuating muscle weakness that may be transiently improved by inhibitors of acetylcholinesterase (AChE) [Penn A. S. and Rowland L. P. (1995) Myasthenia Gravis In: Meritt's Textbook of Neurology, 9th Edition, Williams and Wilkins, Baltimore, section XVII, 754–761]. The characteristic electrodiagnostic abnormality is a progressive, rapid, decline in the amplitude of compound muscle action potentials (CMAP) evoked by repetitive nerve stimulation at 3 or 5 Hz. To date, the standard treatment for MG includes immunosuppressive therapy combined with chronic administration of multiple daily doses of peripheral AChE inhibitors such as pyridostigmine (Mestinon™). While AChE inhibitors effectively restore muscle performance in MG patients, their effects are short-lived, calling for the development of additional effective treatment.

Antisense technology offers an attractive, gene-based alternative to conventional anti-cholinesterase therapeutics. Antisense technology exploits the rules of Watson-Crick base pairing to design short oligonucleotides, 15–25 residues in length, whose sequence is complementary to that of a target mRNA [Agrawal S. and Kandimalla E. R. (2000) Mol. Med. Today, 6, 72–81]. Stretches of double-stranded RNA, resulting from hybridization of the antisense oligonucleotide (ASON) with its target, activate RNAse H [Crooke S. T. (2000) Methods Enzymol. 313, 3–45] and promote specific degradation of the duplex mRNA. As antisense therapeutics target RNA rather than proteins, they offer the potential to design highly specific drugs with effective concentrations in the nanomolar range [Galyam N. et al. (2001) Antisense Nucleic Acid Drug Dev. 11, 51–57]. Phosphorothioated and 3' terminally protected 2'-O-methyl antisense oligonucleotides targeted to mouse AChE mRNA were shown to be effective in blocking AChE expression in vitro in cultured human and rodent cells [Koenigsberger C. et al. (1997) J. Neurochem. 69, 1389–1397; WO 98/26062; Grisaru D. et al. (2001) Mol. Med. 7, 93–105], and in vivo in brain [Shohami E. et al. (2000) J. Mol. Med. 78, 278–236; Cohen et al. (2002) Molecular Psychiatry, in press], muscle [Lev-Lehman E. et al. (2000) J. Mol. Neurosci. 14, 93–105] and bone marrow [Grisaru et al. (2001) ibid.].

The inventors have recently observed that treatment with the irreversible cholinesterase inhibitor diisopropylfluorophosphonate (DFP) induces overexpression of an otherwise rare, non-synaptic alternative splicing variant of AChE, ACHE-R, in brain [Kaufer D. et al. (1998) Nature, 393, 373–377] and intestine [Shapira M. et al. (2000) Hum. Mol. Genet. 9, 1273–1282]. Muscles from animals treated with DFP also overexpressed AChE-R, accompanied by exaggerated neurite branching, disorganized wasting fibers and proliferation of NMJs. Partially protected 2'-O-methyl antisense oligonucleotides targeted to mouse AChE mRNA suppressed feedback upregulation of AChE and ameliorated DFP-induced NMJ proliferation [Lev-Lehman et al. (2000) ibid.]. These observations demonstrated that cholinergic stress elicits overexpression of AChE-R in muscle and that antisense oligonucleotides can suppress such AChE-R excess and prevent its deleterious outcome.

As mentioned above, the characteristic electrodiagnostic abnormality is a progressive, rapid decline in the amplitude of muscle action potentials evoked by repetitive nerve stimulation at 3 or 5 Hz. This myasthenic fatigue is caused by decrease in the number of AChR molecules available at the post-synaptic site. Inhibiting anti-AChR antibodies are present in 85% to 90% of patients [Vincent, A. (1999) id ibid].

Patients with MG, but not with congenital myasthenias due to other causes [Triggs et al. (1992) Muscle Nerve 15, 267–72], display a transient clinical response to AChE inhibitors such as edrophonium. The available anti-AChE drugs are the first line of treatment, but most patients require further help. This includes drastic measures, such as plasma exchange, thymectomy and immunosuppression. Unfortunately, all of the currently employed MG drug regimens are associated with deleterious long-term consequences. These include disturbance of neuromuscular transmission, exacerbation and induction of MG symptoms. Also, the otherwise safe use of common drugs such as anti-infectives, cardiovascular drugs, anticholinergics, anticonvulsants, antirheumatics and others has been reported to worsen the symptoms of MG patients [Wittbrodt (1997) Arch. Intern. Med., 157, 399–408].

While the neuromuscular malfunctioning associated with MG can be transiently alleviated by systemic chronic administration of carbamate acetylcholinesterase (AChE) inhibitors (e.g. pyridostigmine), the inventors have found that pyridostigmine induces a feedback response leading to excess AChE accumulation [Friedman et al. (1996) Nature Medicine 2, 1382–1385; Kaufer et al. (1998) id ibid; Meshorer, E. et al. (2002) *Science* 295, 508–12]. This suggested that the chronic use of such inhibitors would modify the cholinergic balance in the patients' neuromuscular system and would require increased doses of these drugs; it also provided an explanation of the highly variable dose regimen employed in MG patients; and it called for the development of an alternative approach to suppress acetylcholine hydrolysis.

AChE-encoding RNA is subject to 3' alternative splicing yielding mRNAs encoding a "synaptic" (S) isoform, containing exons 1–4 and 6, also designated E6 mRNA herein, an "erythrocytic" (E) isoform, containing exons 1–6, also designated E5 mRNA herein, and the "readthrough" AChE-R derived from the 3'-unspliced transcript, containing exons 1–6 and the pseudo-intron I4, also designated I4 mRNA herein.

Transgenic mice overexpressing human AChE-S in spinal cord motoneurons, but not in muscle, displayed progressive neuromotor impairments that were associated with changes in NMJ ultrastructure [Andres, C. et al. (1997) *Proc. Natl. Acad. Sci. USA* 94, 8173–8178]. However, it was not clear whether the moderate extent of overexpressed AChE in muscle was itself sufficient to mediate this severe myopathology. In rodent brain, the inventors found previously that both traumatic stress and cholinesterase inhibitors induce dramatic calcium-dependent overexpression of AChE-R [Kaufer, et al. (1998) id ibid.], associated with neuronal hypersensitivity to both cholinergic agonists and antagonists [Meshorer et al. (2002) id ibid].

Chronic AChE excess was found to cause progressive neuromotor deterioration in transgenic mice and amphibian embryos [Ben Aziz-Aloya et al. (1993) *Proc. Natl. Acad. Sci. USA*, 90, 2471–2475; Seidman et al. (1994) *J. Neurochem.* 62, 1670–1681; Seidman, et al. (1995) *Mol. Cell. Biol.* 15, 2993–3002; Andres, C. et al. (1997) *Proc. Natl. Acad. Sci. USA* 94, 8173–8178; Sternfeld et al. (1998) *J. Neurosci.* 18, 1240–1249]. Also, myasthenic patients suffer acute crisis events, with a reported average annual incidence of 2.5% [Berrouschot et al. (1997) *Crit. Care Med.* 25, 1228–35] associated with respiratory failure reminiscent of anti-AChE intoxications.

In one approach, the prior art teaches that chemically protected RNA aptamers capable of blocking the autoantibodies to the nicotinic Acetylcholine Receptor (nAChR) may be developed and used to treat MG. This approach has several drawbacks in that the RNA aptamers do not have the amplification power characteristic of the RNAse-inducing antisense agents and in that it fails to address the problem of the feedback responses in MG.

The present inventors have previously found that antisense oligonucleotides against the common coding region of AChE are useful for suppressing AChE production [WO 98/26062]. This publication also teaches that antisense oligonucleotides against the human AChE are useful in the treatment of memory deficiencies as observed in transgenic mice that expressed human AChE in their brain. The observed effects (see Table 4–5 in WO 98/26062) are similar in their effect, yet considerably longer in the duration of their action than the prior art AChE inhibitor tacrine (see FIG. 9B in WO 98/26062).

In view of the above, it is desirable to further improve the treatment approaches for MG and other diseases involving impairment in neuromuscular transmission. The prior art treatment involving the use of AChE inhibitors is afflicted with undesirable side effects because of the induction of AChE and neuromuscular impairments by such inhibitors; and because it is subject to variable efficacy under altered mental state (stress).

WO01/36627 teaches that morphological and functional changes in the NMJ correlate with overexpression of a specific isoform of AChE mRNA, viz., the "readthrough" isoform containing the pseudo-intron I4 in the mature mRNA. Said PCT application also shows that antisense oligonucleotides directed to the common coding region of AChE may be used to specifically destroy AChE-R mRNA, and that AChE antisense agents are by far superior to conventional AChE enzyme inhibitor drugs in the treatment of neuromuscular disorders. The superiority of these antisense agents may be due to the fact that conventional enzyme inhibitors actively induce I4 AChE mRNA overexpression. According to the teachings of WO01/36627, this may lead to detrimental changes in the NMJ. This consequence of treatment may be entirely avoided by using the antisense agents of WO01/36627.

The Blood-Brain Barrier (BBB) maintains a homeostatic environment in the central nervous system (CNS). The capillaries that supply the blood to the brain have tight junctions which block the passage of most molecules through the capillary endothelial membranes. While the membranes do allow passage of lipid soluble materials, water soluble materials do not generally pass through the BBB. Mediated transport mechanisms exist to transport the water soluble glucose and essential amino acids through the BBB. Active support mechanisms remove molecules which become in excess, such as potassium, from the brain [for general review see Betz et al., Blood-Brain-Cerebrospinal Fluid Barriers, Chapter 32, in Basic Neurochemistry, 5$^{th}$ ed., Eds Siegel, Albers Agranoff, Molinoff, pp.681–701; Goldstein and Betz (1986) *Scientific American*, September, pp. 74–83].

The BBB impedes the delivery of drugs to the CNS. Methods have been designed to deliver needed drugs such as direct delivery within the CNS by intrathecal delivery can be used with, for example, an Omaya reservoir. U.S. Pat. No. 5,455,044 provides for the use of a dispersion system for CNS delivery [for description of other CNS delivery mechanisms, see U.S. Pat. No. 5,558,852, Betz et al., ibid., and Goldstein and Betz, ibid.]. Tavitan et al. [Tavitan et al. (1998) *Nat Med* 4(4): 467–71] observed that 2'-O-methyl oligonucleotides are able to penetrate into the brain. Other systems make use of specially designed drugs that utilize the structure and function of the BBB itself to deliver the drugs, for example by designing lipid soluble drugs or by coupling to peptides that can penetrate the BBB.

It has been shown that stress affects the permeability of the BBB [Sharma H. S. et al. (1992) *Prog. Brain Res.* 91, 189–196; Ben-Nathan D. et al. (1991) *Life Sci.* 489, 1493–1500]. Further, in mammals, acute stress elicits a rapid, transient increase in released acetylcholine with a corresponding phase of increased neuronal excitability [Imperato A. et al. (1991) *Brain Res.* 538, 111–117]. It has been previously observed by the present inventors that the AChE-R isoform and the I4 peptide of AChE can act as stress mimicking agents and rupture the BBB. These findings formed the basis for PCT application WO98/22132, the contents of which are fully incorporated herein by reference. WO98/22132 relates to compositions for facilitating the passage of compounds through the BBB, comprising the AChE-R splice variant and/or the peptide I4.

In search for an antisense oligonucleotide targeted against a domain of the human AChE, which may be particularly acceptable in human therapy, the inventors have now found, and this is an object of the present invention, that a synthetic antisense oligodeoxynucleotide having the nucleotide sequence: 5'-CTGCCACGTTCTCCTGCACC-3', herein designated SEQ ID NO:1, is not only useful in selectively suppressing the production of the AChE-R isoform, but also possesses cross-species specificity, which enables its use in rodent animal models of various diseases and, moreover, remarkably appears to penetrate the BBB, and may thus be useful in treatment of diseases of the central nervous system, alone or in combination with other therapeutic agents. The finding that the novel antisense of the invention can penetrate the BBB was unexpected, particularly in view of the expectation that the BBB would be impermeable to large polar molecules.

The application of antisense technology to the treatment of nervous system disorders has, until recently, been considered to be limited by the lack of adequate systems for delivering oligonucleotides to the brain. Nevertheless, several attempts have been made to circumvent this difficulty [reviewed in Seidman S. et al. (1999) *Antisense Nucl. Acid Drug Devel*, 9, 333–340]. Access of chemical agents circulating in the blood to the interstitial spaces of the brain is restricted by the biomechanical barrier known as the BBB. The strong anionic character of the phosphodiester backbone makes oligonucleotides especially poor at crossing the BBB. In vivo pharmacokinetic studies have demonstrated that less than 0.01% of a systemically injected dose of a phosphorothioate antisense oligonucleotide may reach the brain, where its residence time may be as little as 60 min. A research solution to this problem in the laboratory is direct bypass of the BBB by intracranial injection of oligonucleotides. Using published stereotactic coordinates for both rats and mice, oligonucleotides can be delivered by single injections, by repeated administration through an implanted cannula, or by continuous infusion using an osmotic mini-pump such as Alzet (Alza, Palo Alto, Calif.). Oligonucleotides can either be delivered into the CSF or directly into the brain region of interest. In general, oligonucleotides are considered to remain relatively localized following intraparenchymal administration. Thus, a single injection of 24 µg of an antisense oligonucleotide targeted to the cAMP-response element (CREB) into rat amygdala was reported to diffuse only 0.72±0.04 µl around the injection site, exerting region-specific effects on conditioned taste aversion (CTA). Injection of the same oligonucleotide into the basal ganglia 2 mm above the amygdala had no effect on CTA. Similarly, specific effects on behavior were reported following the injection of antisense oligonucleotides against the stress-associated transcription factor c-fos into the medial frontal cortex (single administration; 10 µg), following delivery of oligonucleotides against the neurotransmitter-synthesizing enzyme glutamate decarboxylase into the ventromedial hypothalamus (single administration; 1 µg), and following 5 days continuous infusion of oligonucleotides targeted to mRNA encoding the cAMP-responsive transcription factor CREB into the locus coeruleus (20 µg/day). It was further reported that wide distribution of oligonucleotides in the brain (up to 443 µl around the site of injection after 48 hrs) could be achieved by direct, high-flow intraparenchymal microinfusion. In that case, the average tissue concentration of oligonucleotide was calculated to be between 3–15 µM—well within what is considered physiologically significant. Regarding uptake into neurons, it was shown that neurons in the striatum of rats preferentially take up oligonucleotides compared to glia. Despite the general retention of oligonucleotides around the injection site reported in that study, some signal was observed to be transported along projection pathways to distant sites. However, to be effective therapeutically, oligonucleotides should be prepared in a way that would enable their stability and free penetrance into the central nervous system following intravenous injection, or yet more preferably, following oral administration. Thus, the present invention is aimed at a novel, preferably nuclease protected antisense oligodeoxynucleotide targeted to the common coding domain of human AChE, which selectively suppresses the production of AChE-R, with rapid and long-lasting clinical improvements in muscle function, which possesses cross-species specificity and can penetrate the BBB and destroy AChE-R mRNA within central nervous system neurons.

SUMMARY OF THE INVENTION

The invention relates to a pharmaceutical or medical composition for the treatment and/or prevention of a progressive neuromuscular disorder, comprising as active ingredient a synthetic antisense oligodeoxynucleotide targeted against human AChE mRNA having the nucleotide sequence:
5' CTGCCACGTTCTCCTGCACC 3' (SEQ ID NO:1).

The antisense oligonucleotide preferably causes preferential destruction of AChE-R mRNA, possesses cross-species specificity, was demonstrated to cause no toxicity in rodents or primates, and can penetrate the BBB in primates (monkeys) via both i.v. and p.o. administration routes.

In a preferred embodiment, the synthetic antisense oligodeoxynucleotide having the nucleotide sequence designated SEQ ID NO:1 is nuclease resistant. The nuclease resistance may be achieved by modifying the antisense oligodeoxynucleotide of the invention so that it comprises partially unsaturated aliphatic hydrocarbon chain and one or more polar or charged groups including carboxylic acid groups, ester groups, and alcohol groups.

In particular embodiments, the nuclease resistant antisense oligodeoxynucleotide of the invention has at least one of the last three 3'-terminus nucleotides is 2'-O-methylated, preferably the last three 3'-terminus nucleotides are 2'-O-methylated. Alternatively, the nuclease resistant antisense oligodeoxynucleotide of the invention may have at least one of the last 3'-terminus nucleotides fluoridated. Still alternatively, the nuclease resistant antisense oligodeoxynucleotide of the invention has phosphorothioate bonds linking between at least two of the last 3'-terminus nucleotide bases, preferably has phosphorothioate bonds linking between the last four 3'-terminal nucleotide bases. Still alternatively, nuclease resistance may be achieved by the synthetic nuclease resistant antisense oligodeoxynucleotide of the invention having a nucleotide loop forming sequence at the 3'-terminus, for example a 9-nucleotide loop having the nucleotide sequence CGCGAAGCG (SEQ ID NO:2).

The synthetic nuclease resistant antisense oligodeoxynucleotide of the invention is capable of selectively modulating mammalian AChE production, particularly selectively modulating primate AChE production in neurons residing in the central nervous system, including human AChE of interneurons.

In a further aspect, the invention relates to a pharmaceutical composition comprising an antisense oligodeoxynucleotide of the invention, and optionally further comprising pharmaceutically acceptable adjuvant, carrier or diluent.

In a preferred embodiment, the pharmaceutical composition of the invention comprises an antisense oligodeoxynucleotide of SEQ ID NO:1, which is 2'-O-methylated on at least one, preferably the three last 3'-terminus nucleotides.

The pharmaceutical composition of the invention is useful in the treatment and/or prevention of a progressive neuromuscular disorder, for improving stamina and/or for use in decreasing chronic muscle fatigue.

The pharmaceutical composition of the invention may be for a once daily use by a patient of a dosage between about 0.001 µg/g and about 50 µg/g of active ingredient, preferably a dosage of active ingredient of about 0.01 to about 5.0 µg/g, more preferably a dosage of active ingredient of about 0.15 to about 0.5 µg/g.

The pharmaceutical composition of the invention is particularly intended for use in treating or preventing a progressive neuromuscular disorder, wherein said disorder is associated with an excess of AChE mRNA or protein. Such a disorder may be, for example, a progressive neuromuscular disorder, wherein said disorder is associated with an excess of AChE-R mRNA.

The pharmaceutical composition of the invention is thus particularly suitable for treating or preventing a progressive neuromuscular disorder, wherein said disorder is associated with impairment of cholinergic transmission.

Of particular interest are pharmaceutical compositions for the treatment of a progressive neuromuscular disorder, wherein said disorder involves muscle distortion, muscle re-innervation or NMJ abnormalities, for example myasthenia gravis, Eaton-Lambert disease, muscular dystrophy, amyotrophic lateral sclerosis, post-traumatic stress disorder (PTSD), multiple sclerosis, dystonia, post-stroke sclerosis, post-injury muscle damage, post-surgery paralysis, excessive re-innervation, and post-exposure to AChE inhibitors.

The pharmaceutical composition of the invention is also useful in improving stamina in physical exercise or in decreasing muscle fatigue.

In addition, the invention relates to a pharmaceutical composition comprising an antisense oligodeoxynucleotide as denoted by SEQ ID NO:1, for facilitating passage of compounds through the BBB, optionally further comprising additional pharmaceutically active agent and/or pharmaceutically acceptable adjuvant, carrier or diluent. The additional pharmaceutically active agent is a compound to be transported through the BBB, wherein said compound may be contrast agents used for central nervous system imaging, agents that function to block the effects of abused drugs, antibiotics, chemotherapeutic drugs and vectors to be used in gene therapy. This composition would function primarily by suppressing the production of AChE-R, which is apparently involved in BBB maintenance.

The invention will be described in more detail in the following detailed description and on hand of the following figures.

BRIEF DESCRIPTION OF THE FIGURES

FIG. 1 Human AChE cDNA [GenBank Accession No. M55040; Soreq et at., *Proc. Natl. Acad. Sci. USA* 87(24), 9688–9692 (1990); SEQ ID NO:7], and human EN101 (hEN101, SEQ ID NO:1), targeted at nucleotides 795-5' to 3'-814 (shaded; SEQ ID NO:10) of the coding sequence.

FIG. 2A–B Representation of various physical and chemical properties of the human EN101 (SEQ ID NO:1).

FIG. 2A: Internal structure that is expected for the oligonucleotide, and an estimate of the energy (in kcal/mol) required to disrupt that structure.

FIG. 2B: Base composition and the predicted melting temperature of its hybrid with the complementary mRNA.

FIG. 3 Mouse AChE cDNA [GenBank Accession No. X56518; Rachinsky et al. (1990) *Neuron* 5(3), 317–327; SEQ ID NO:8], and mouse EN101 (mEN101, SEQ ID NO:3), targeted at nucleotides 639-5' to 3'-658 (shaded; SEQ ID NO: 11) of the coding sequence.

FIG. 4A–B Representation of various physical and chemical properties of the mouse EN101 (SEQ ID NO:3).

FIG. 4A: Internal structure that is expected for the oligonucleotide, and an estimate of the energy (in kcal/mol) required to disrupt that structure.

FIG. 4B: Base composition and the predicted melting temperature of its hybrid with the complementary mRNA.

FIG. 5 Rat AChE cDNA (partial, 2066 nucleotides) [GenBank Accession No. S50879; Legay et al. (1993), *J. Neurochem.* 60(1), 337–346; SEQ ID NO:9], and the rat EN102 (rEN102SEQ ID NO:5), targeted at nucleotides 51-5' to 3'-70 (shaded; SEQ ID NO: 13) and rat EN101 (rEN101, SEQ ID NO:4), targeted at nucleotides 639-5' to 3'-658 (shaded; SEQ ID NO:12) of the coding sequence.

FIG. 6A–B Representation of various physical and chemical properties of the rat EN101 (SEQ ID NO:4).

FIG. 6A: Internal structure that is expected for the oligonucleotide, and an estimate of the energy (in kcal/mol) required to disrupt that structure.

FIG. 6B: Base composition and the predicted melting temperature of its hybrid with the complementary mRNA.

Separation of rat serum was performed in non-denaturing polyacrylamide gel, and the gel tested for immunoreactive AChE-R. An EAMG rat had considerably higher level of the rapidly migrating rR variant than a control rat.

Abbreviations: electroph., electrophoresis; cont., control.

Figure 8A:
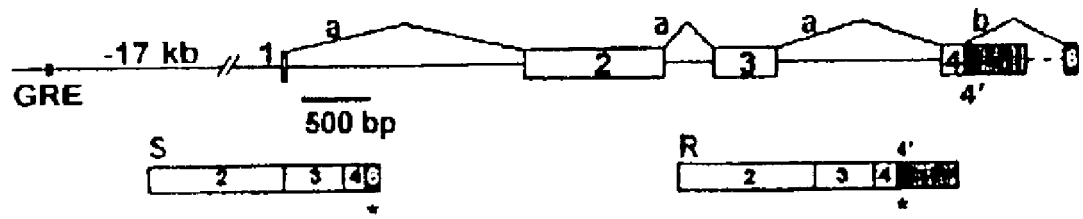
Figure 8B:
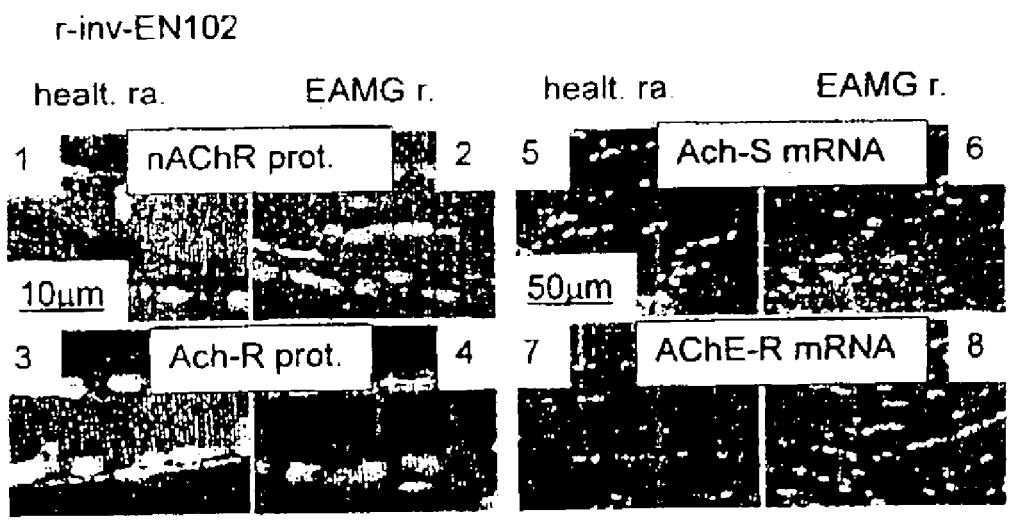
Figure 8C:
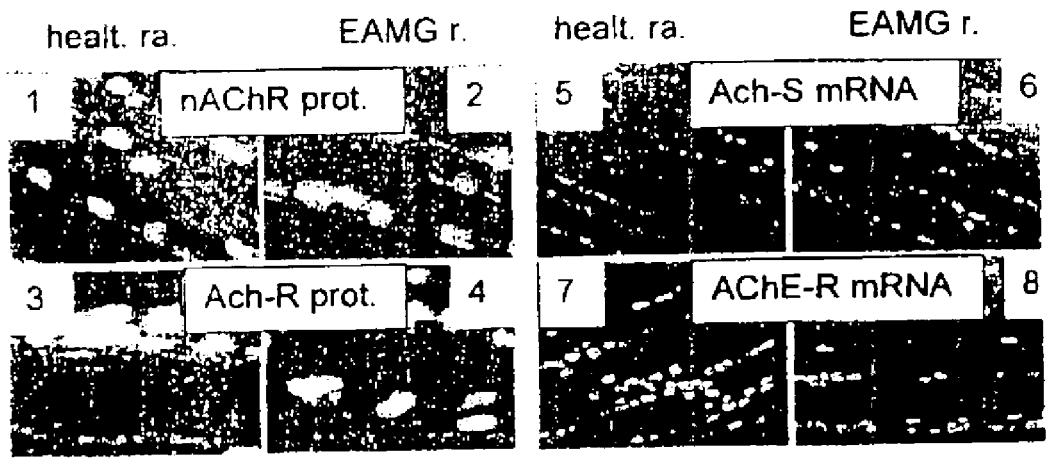

FIG. 8A–C Excess AChE-R expression in muscles of EAMG rats.

FIG. 8A: AChE mRNA transcripts expressed in muscle. Shown is the stress-responding mammalian ACHE gene, with a functional glucocorticoid response element (GRE) in its distal enhancer, and its two mRNA transcripts expressed in muscle. Note that exon 6 is unique to the synaptic transcript AChE-S, whereas, pseudo-intron 4' is expressed only in the stress induced AChE-R mRNA. Antibodies targeted to the pseudo-intron 4'-derived C-terminal peptide served to detect the AChE-R protein, and cRNA probes to exon 6 and pseudo-intron 4' label the two transcripts (asterisks).

FIG. 8B: Depleted nAChR and excess AChE-R in EAMG muscles. Shown is immunohistochemical staining of paraffin-embedded sections of triceps muscle from normal or EAMG rats treated with the inert inverse (r-invEN102) oligonucleotides, similar to those of untreated rats. Staining was with polyclonal rabbit antibodies to nAChR (1,2) and AChE-R (3,4). Immunopositive areas are stained red. Note that the AChE-R protein was prominently elevated and nAChR dramatically reduced in EAMG. In situ hybridization with probes specific for AChE-R or -S mRNAs yielded red stained RNA, with DAPI (white) used to visualize cell nuclei. Note the prominent sub-nuclear accumulation of AChE-R mRNA in preparations from EAMG, but not control animals (5,6). AChE-S mRNA displayed punctuated expression in sub-nuclear areas in both control and EAMG rats (7,8).

FIG. 8C: rEN101 treatment. In EAMG rats, EN101 reduced levels of AChE-R (1,2) and AChE-R mRNA (5,6), but did not affect nAChR (3,4) or AChE-S mRNA (7,8), as compared to rats treated with the inverse sequence (see FIG. 8B, above.).

Abbreviations: healt., healthy; r., rat; prot., protein.

FIG. 9A–D Normalized EAMG muscle electrophysiology under suppression of AChE-R.

Figure 9A:
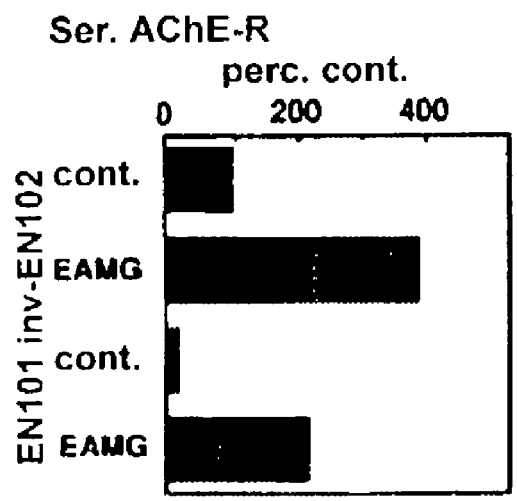

FIG. 9A: Immunoreactive AChE-R was detected, as in FIG. 7B, in the serum of healthy and severely affected EAMG rats, treated with rEN101 or r-invEN102, and the densities of the bands are represented in the bar graph.

Figure 9B:
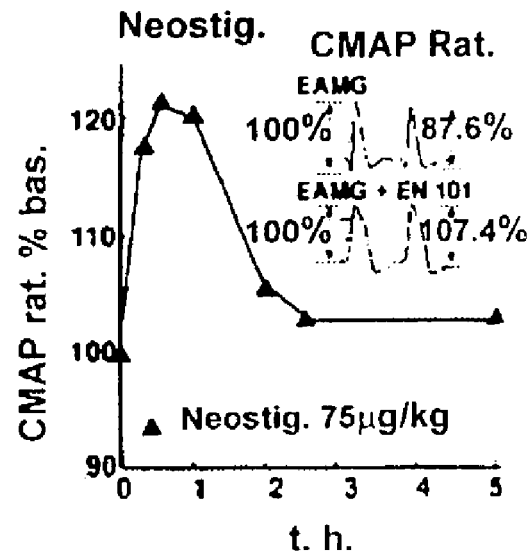

FIG. 9B: Animals (at least 6 rats in each group) were treated with a single i.p. injection (75 µg/kg) of the AChE inhibitor neostigmine, and the CMAP ratio relative to the baseline was measured. The average CMAP ratio of EAMG rats included in the study prior to treatment was 87±2.5% of first depolarization, and average CMAP ratio in rEN101-treated animals was 107.4±3.8% (inset).

Figure 9C:
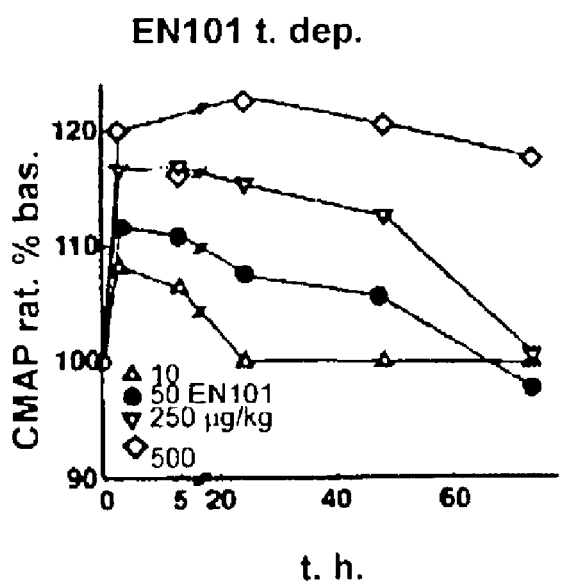

FIG. 9C: Animals (at least 6 rats in each group) were treated with various doses of rEN101. The treatment (doses between 10–500 µg/Kg) restored the CMAP decline for up to 72 h. Note that higher doses conferred increasingly longer-lasting relief.

Figure 9D:
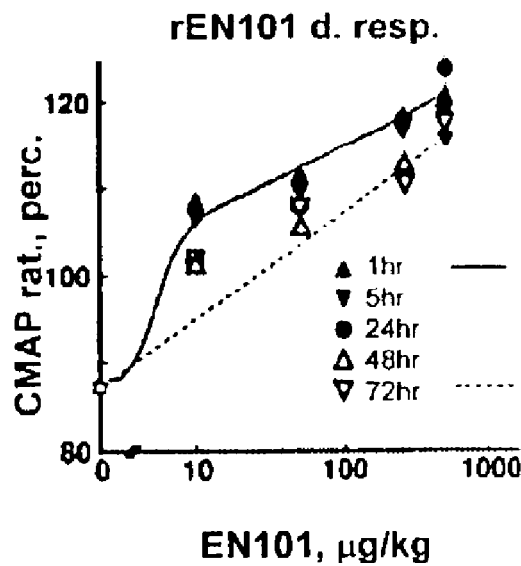

FIG. 9D: Dose response curse. CMAP responses at each time were plotted as a function of EN101 concentration. Note that at 1 and 5 h there are clearly two effects, a steep increase dependent on a low EN101 concentration ($IC_{50}<10$ µg/kg), superimposed on a much lower-affinity effect that persists much longer.

Abbreviations: ser., serum; t., time; dep., dependence; neostig., neostigmine; resp., response; h., hours; perc., percent; cont., control; rat., ratio; bas., baseline.

Figure 10:
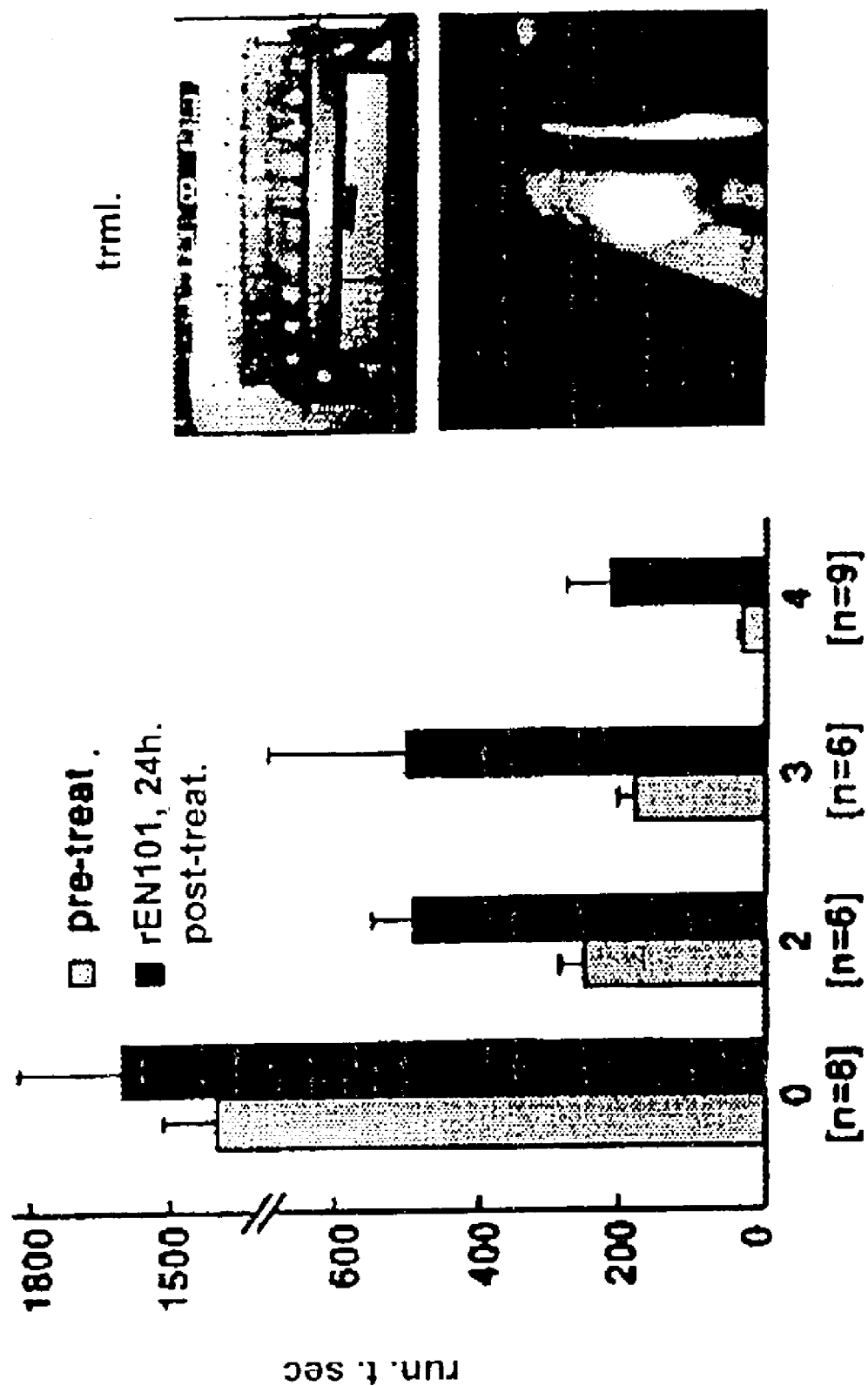

FIG. 10 Rat EN101 (SEQ ID NO:4) improves stamina in myasthenic rats.

Experimental autoimmune myasthenic gravis (EAMG) rats with varying severity of clinical symptoms and healthy Lewis rats were prodded to run on an electrically powered treadmill (25 m/min, inset) until visibly fatigued. Presented is the average time (sec.±SEM) rats were able to run before and 24 h following i.v. administration of 250 µg/kg rEN101. Note that running time for EAMG rats decreased with disease severity, and increased for each group treated with rEN101.

Abbreviations: trml., treadmill; treat., treatment; h., hour; clin., clinical; stat., status; run., running; t., time; sec., seconds.

Figures 11A, 11B:
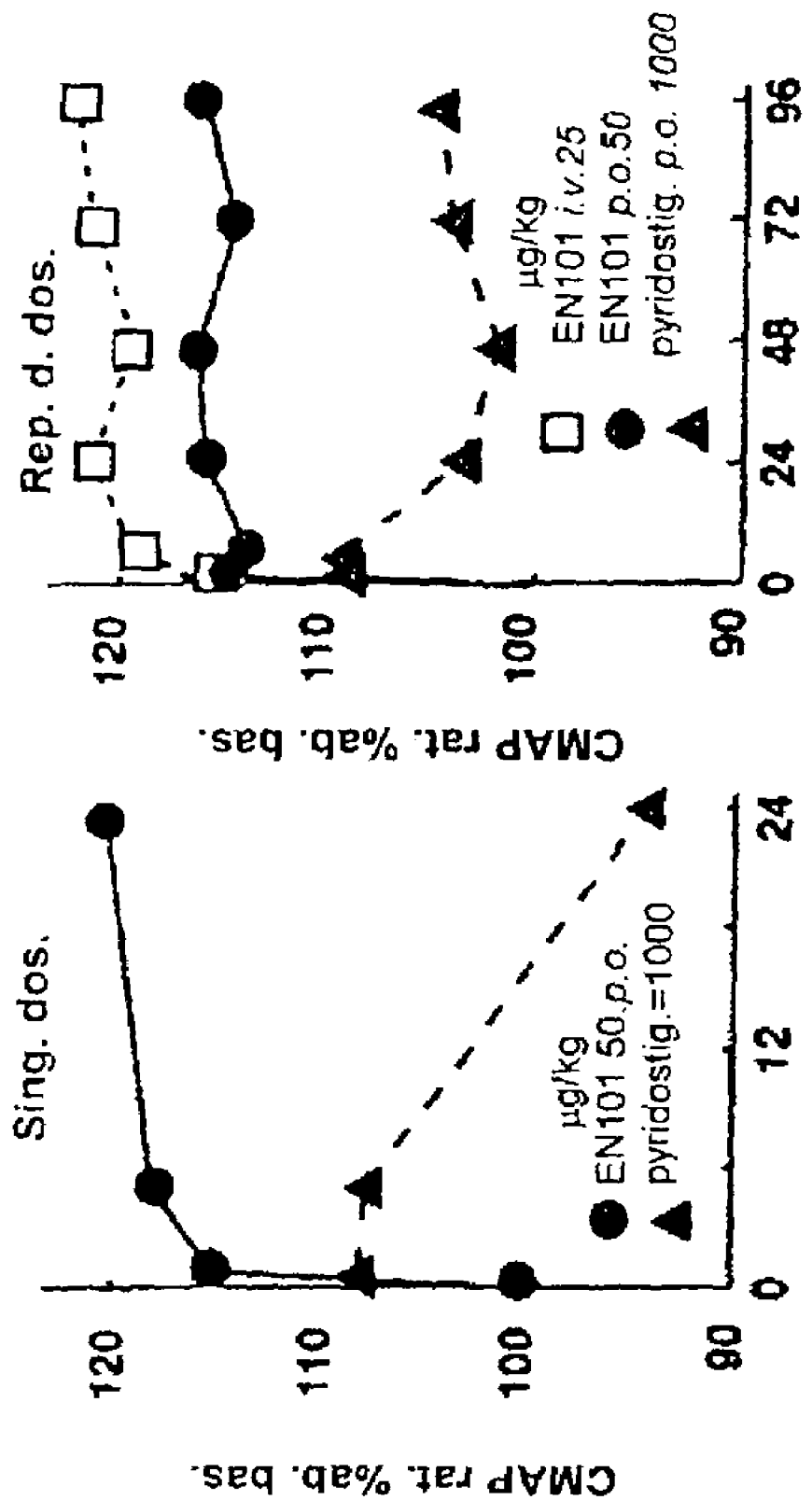

FIG. 11A–B Stable reversal of declining CMAP response in EAMG rats treated orally with rEN101.

EAMG rats received rEN101 once daily for up to 4 days by intravenous injection (25 µg/kg) or via oral gavage (50 µg/kg), or pyridostigmine (1000 µg/kg) by oral gavage. The CMAP ratio was determined 1 and 5 h following the first drug administration and then every 24 h, prior to the administration of the subsequent dose.

FIG. 11A: Single dose. Orally administered pyridostigmine (n=4) and rEN101 (n=8) relieved the declining CMAP responses within 1 h. 24 h following administration of pyridostigmine, CMAP ratios in muscles of treated rats returned to the declining baseline. In contrast, no decline was detected in rats treated with rEN101.

FIG. 11B: Repeated daily doses. The graph depicts the equivalent improvement in muscle function elicited by oral (50 µg/kg, n=8) as compared to i.v. (25 µg/kg, n=4) administration of rEN101. Note that repeated administration of rEN101 conferred stable, long-term alleviation of CMAP declines. Repeated daily administration of pyridostigmine at 24 h intervals yielded considerably shorter CMAP improvements than those obtained with EN101, decreasing back to the declining baseline prior to the next dose.

Abbreviations: sing., single; dos., dose; rep., repeated; d., daily; pyridostig., pyridostigmine; h., hours; rat., ratio; bas., baseline; ab., above.

Figures 12A, 12B, 12C:
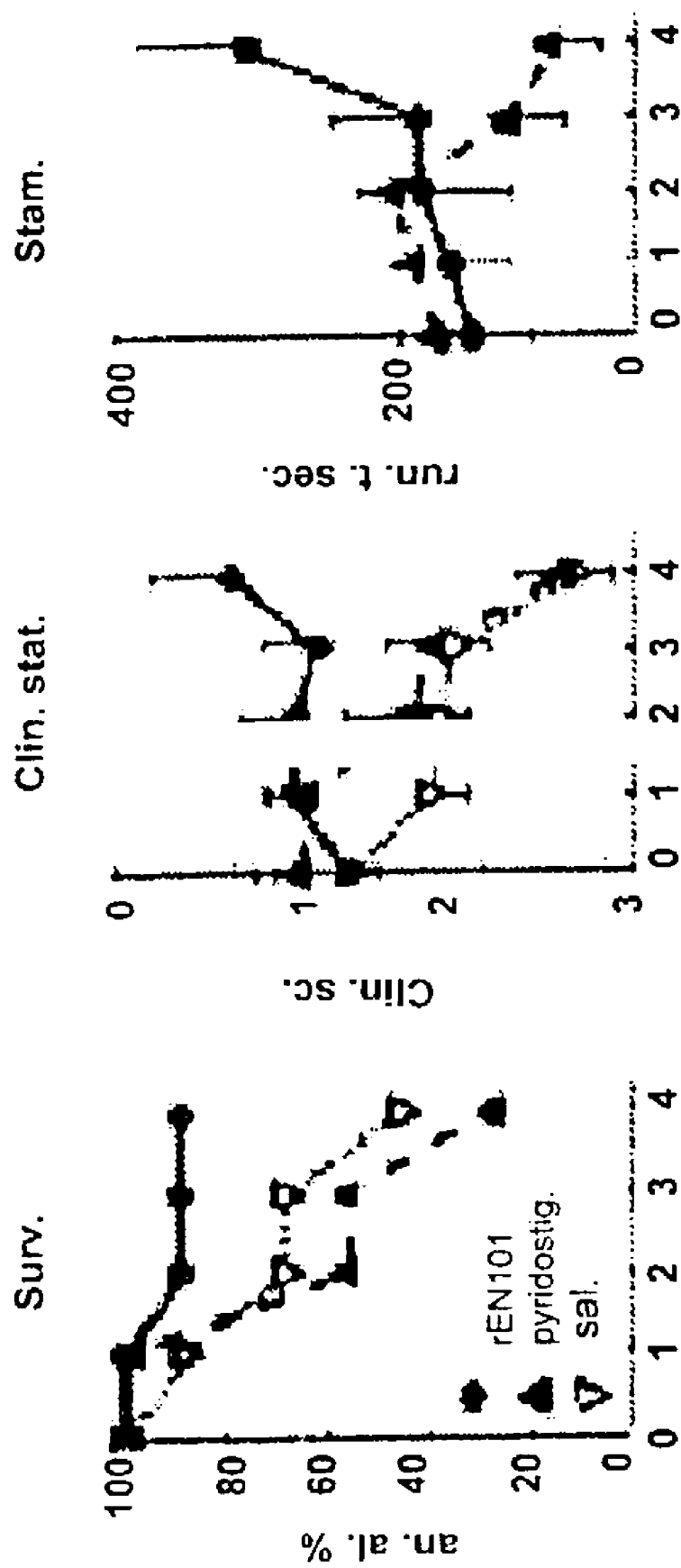

FIG. 12A–C: Long-term rEN101 treatment changes the course of EAMG.

FIG. 12A: Survival. A greater fraction of animals treated once daily with rEN101 (50 µg/Kg, daily, p.o.) survived than those treated with pyridostigmine (1000 µg/Kg) despite their similarly poor initial status and initial number of animals in each group.

FIG. 12B: Clinical status. Shown are average values for the clinical status (as defined in Experimental Procedures) of surviving animals from each of the treated groups. Note increasing severity of disease in saline- and pyridostigmine-treated animals, as compared to the improved status of rEN101-treated animals.

FIG. 12C: Stamina. Shown are average running times in sec. for rEN101- and pyridostigmine-treated animals. Note that before treatment, EAMG rats performed as severely sick animals (clinical status 4).

Abbreviations: surv., survival; clin., clinical; stat., status; stam., stamina; an., animals; al., alive; sc., score; run., running; t., time; sec., seconds; w., weeks; sal., saline; pyridostig., pyridostigmine.

Figure 13:
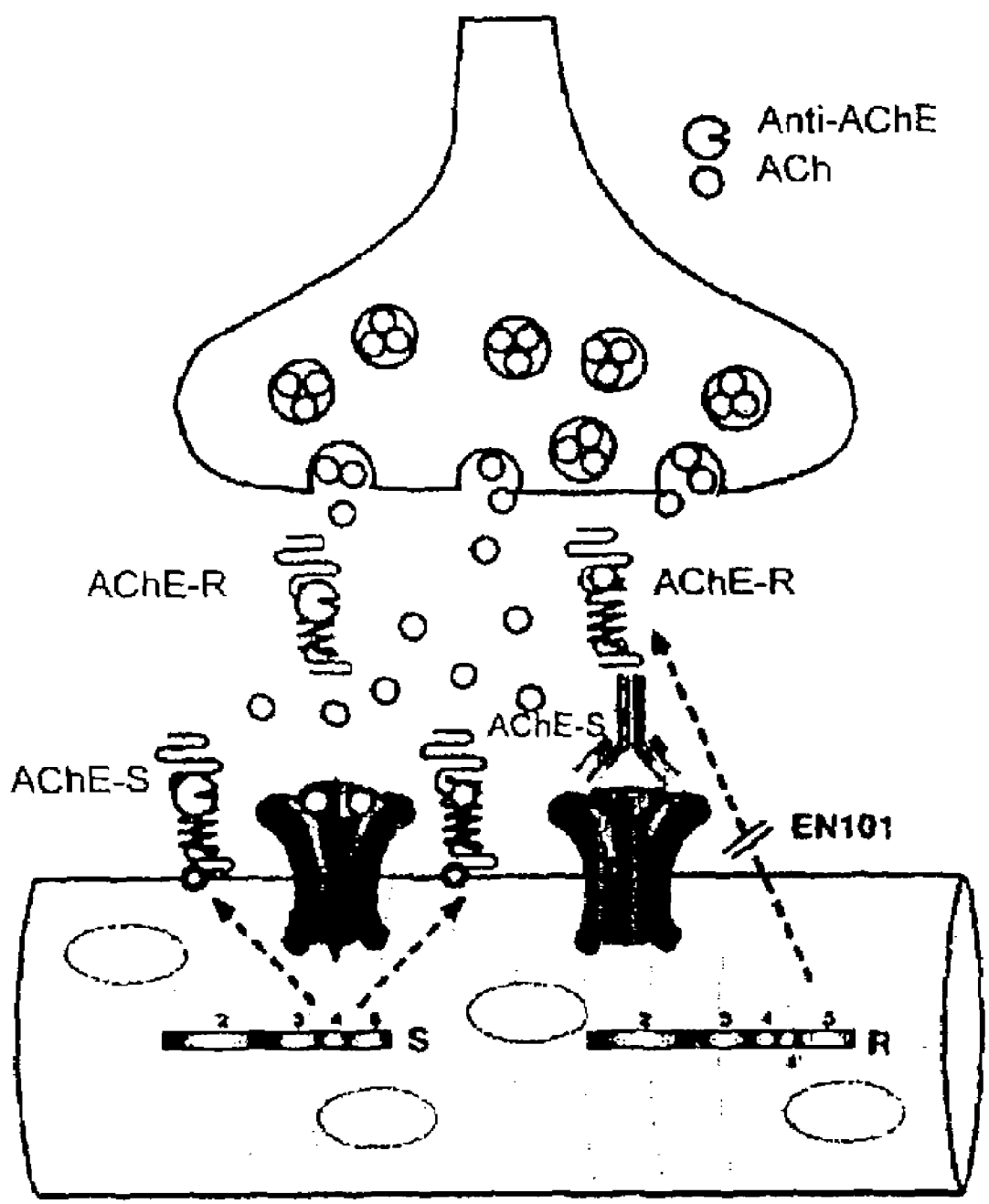

FIG. 13 Proposed model for EN101 activity

At the neuromuscular junction, acetylcholine (ACh) released from the motoneuron terminal (top) into the synaptic cleft travels towards the muscle postsynaptic membrane (below). There, it interacts with nAChR to initiate an inward ion current and elicit muscle action potentials. ACh is subsequently hydrolyzed by synapse-bound AChE-S. Subsynaptic muscle nuclei (ellipses) produce, in addition to the primary AChE-S mRNA transcript, the normally rare AChE-R mRNA with its alternative 3'-end. This transcript translates into soluble, secretory AChE-R monomers. Myasthenic autoimmune antibodies toward nAChR block the initiation of action potentials, mimicking an ACh-deficient state. The cholinergic imbalance results in AChE-R accumulation that enhances ACh destruction, leading to muscle fatigue. Chemical anticholinesterases (indented circles) non-selectively block both AChE-S and AChE-R, which transiently increases ACh levels, yet further intensifies AChE-R overproduction. In contrast, the antisense agent EN101 selectively induces AChE-R mRNA destruction, preventing AChE-R synthesis while maintaining AChE-S and sustaining normal neuromuscular transmission.

Figure 14:
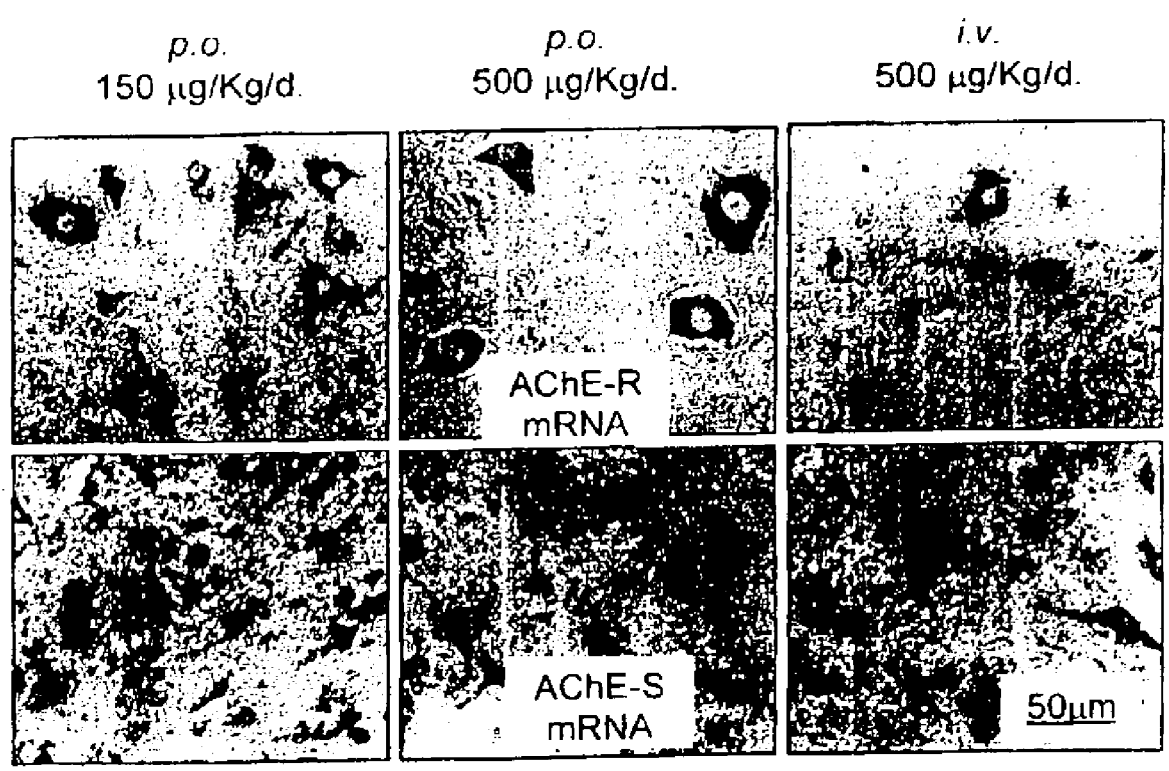

FIG. 14 Dose-dependent hEN101 suppression of neuronal AChE-R mRNA, but not of AChE-S mRNA.

Shown are representative fields from spinal cord sections of hEN101-treated monkeys following in situ hybridization with AChE-R or AChE-S cRNA probes. Note that AChE-R mRNA labeling decreased, but AChE-S mRNA levels appeared unchanged. An increasing dose of o.g.-administered hEN101 suppressed AChE-R mRNA more effectively, suggesting dose-dependence. Administration of the higher dose via i.v. appeared more effective than the o.g. route.

Abbreviations: d., day.

Figure 15:
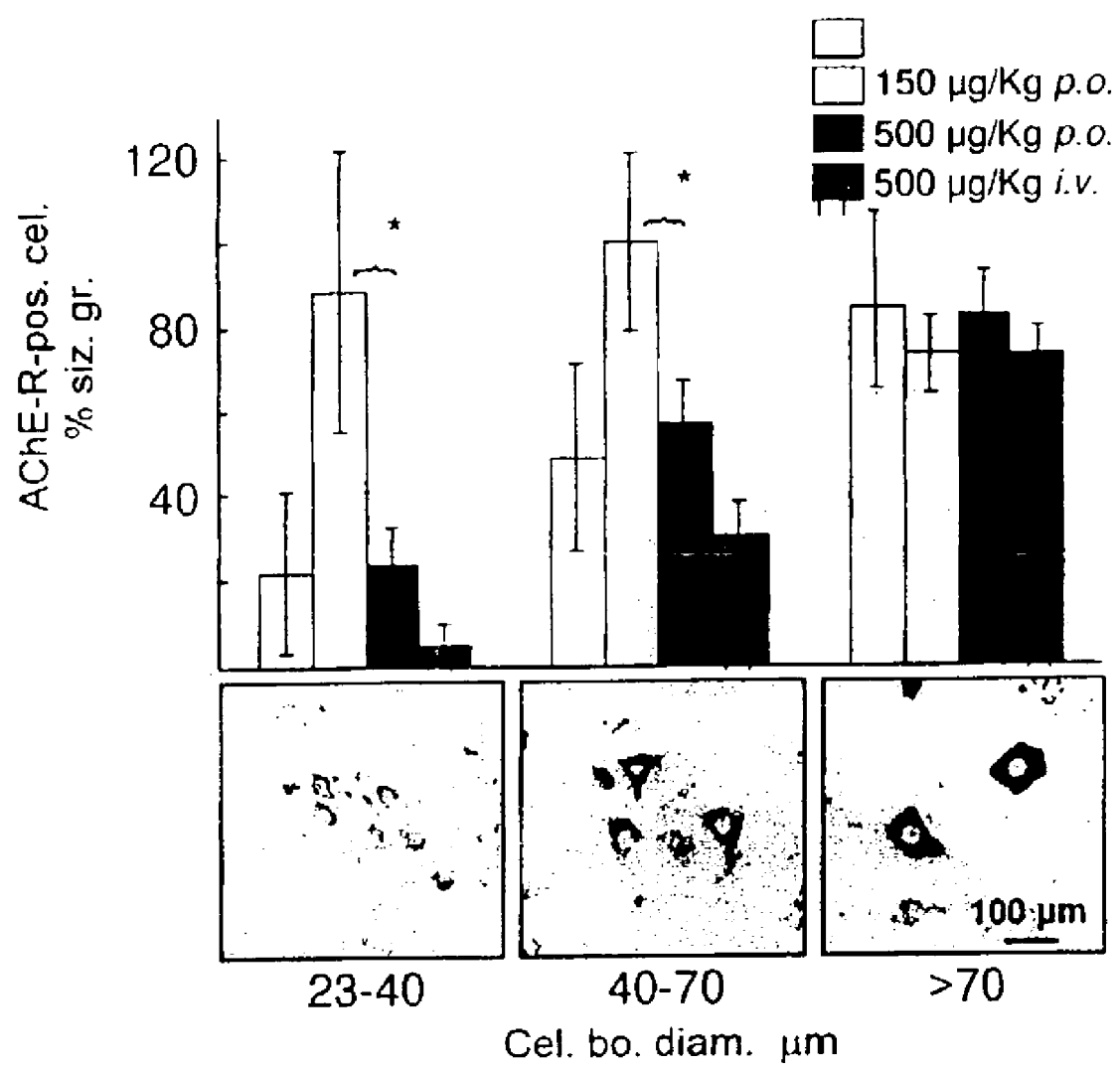

FIG. 15 hEN101-suppression of neuronal AChE-R mRNA levels is cell type-specific.

Spinal cord neurons from hematoxylin-eosin stained monkey sections were divided by size into cells with perikaryal diameters of <40, 40 to 70 and >70 µm. The percent of cells within each size group that were positively labeled for AChE-R mRNA was recorded in 5 different fields of 1 mm$^2$ each, for each hEN101 treatment. Note that hEN101 effectiveness was apparently highest in the relatively small interneurons, and lowest in the largest motoneurons.

Abbreviations: pos., positive; cel., cell; siz., size; gr., group; bo., body; diam., diameter; nv., naive.

Figures 16A, 16B:
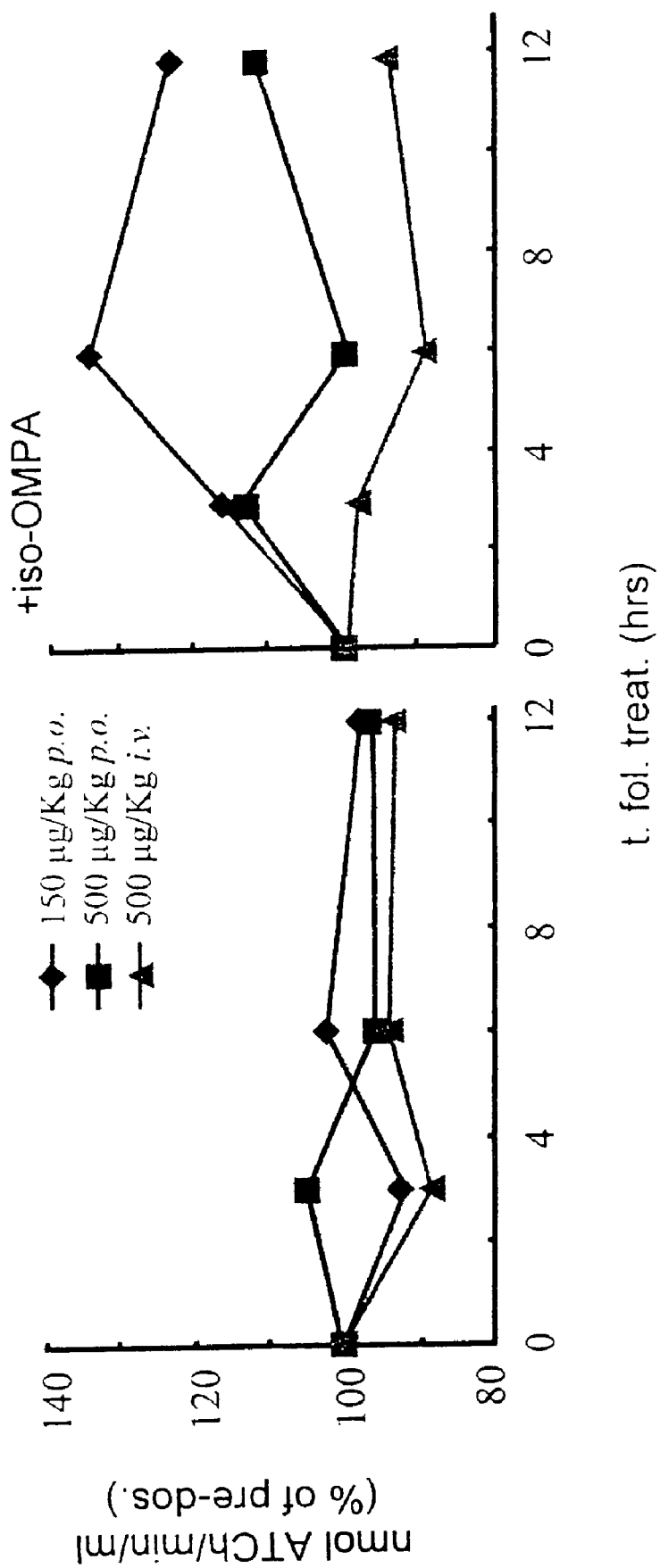

FIG. 16A–B Shown are levels of hydrolyzed acetylcholine, indicating acetylcholinesterase activity in the plasma of cynomolgous monkeys treated orally for two consecutive days with 150 or 500 µg/kg hEN101 or with 500 µg/kg hEN101 administered via i.v.

FIG. 16A: Total activity.

FIG. 16B: Activity under $5 \times 10^{-5}$ M of iso-OMPA (AChE). Note injection-induced increases in enzyme activity and AS-ON reductions.

Abbreviations: t., time; fol., following; treat., treatment hrs., hours.

Figure 17:
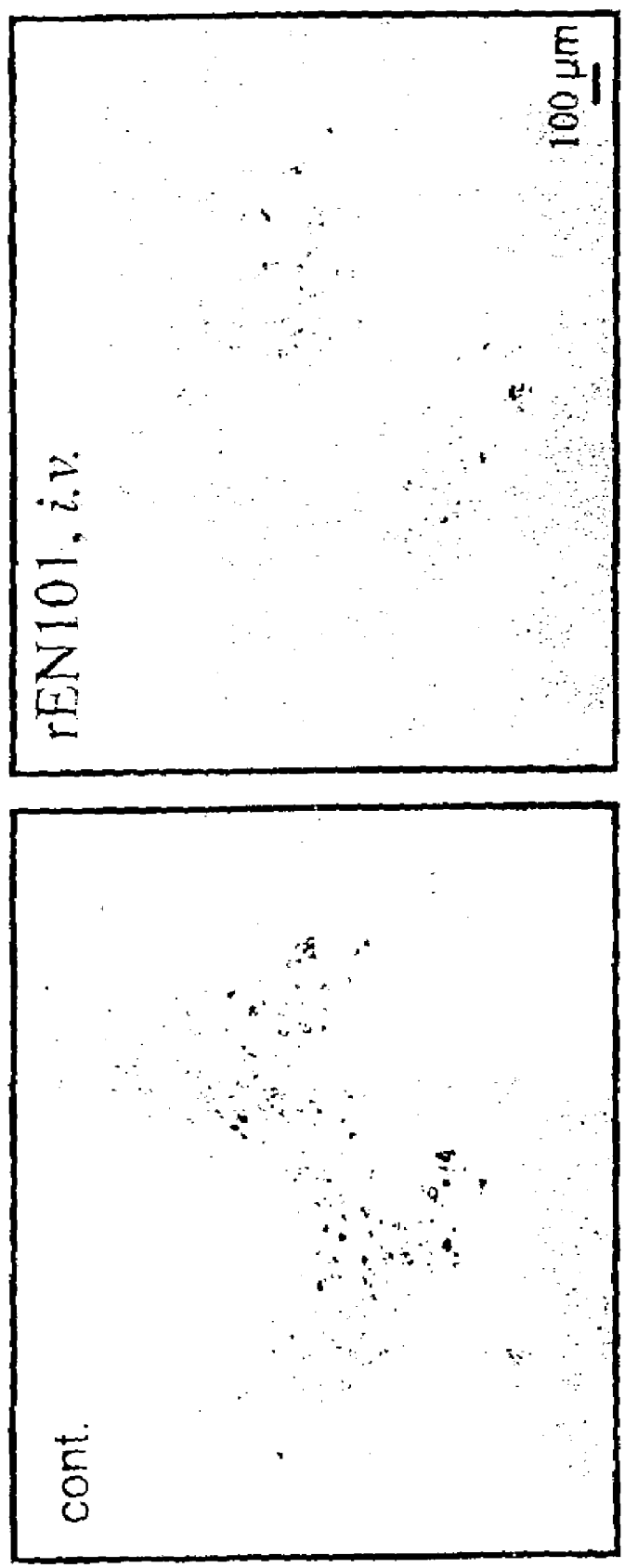

FIG. 17 Effect of rEN101 on AChE-R mRNA in rat spinal cord neurons. The presence of AChE-R mRNA-positive cells was determined in spinal cord section of rats that had been treated for 7 days with rEN101 (500 µg/kg, i.v., daily).

Abbreviations: cont., control.

Figure 18:
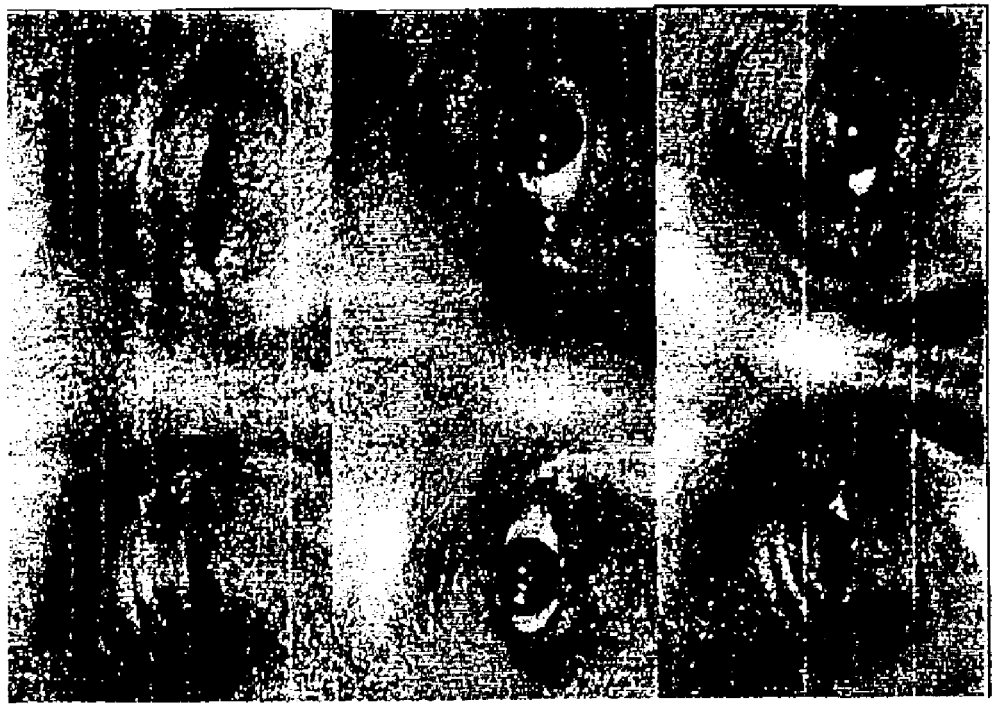

FIG. 18 hEN101 alleviates ptosis in MG patients. Photographs show: before hEN101 treatment (upper panel), on 10 Mestinon®/day, 600 mg; during hEN101 treatment (middle panel), 500 µg/kg, 2-day treatment; and 4 weeks after hEN101 treatment (lower panel), back to Mestinon® treatment.

Figure 19:
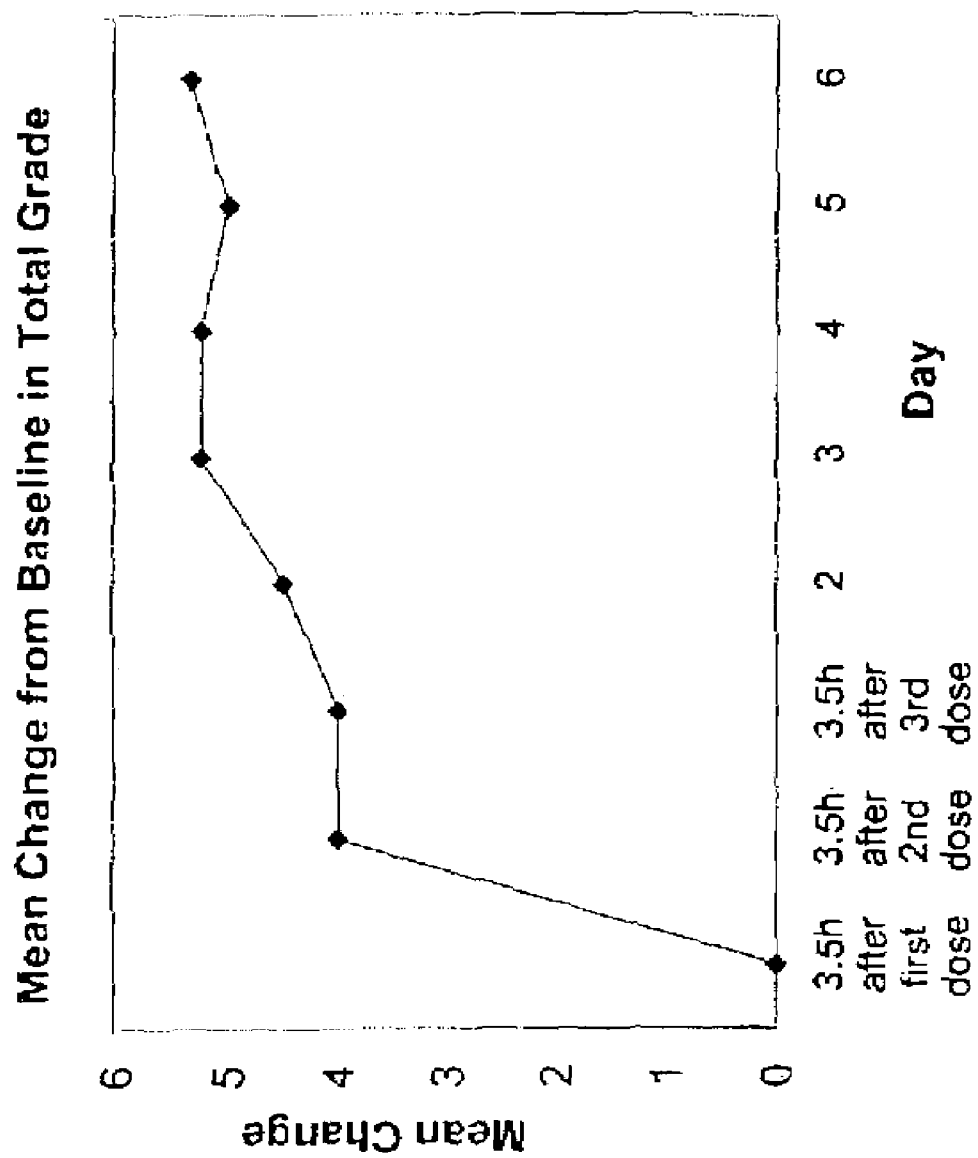

FIG. 19 Efficacy of oral hEN101 in MG patients. Graph shows mean change from baseline of one patient in total grade. This patient was a 56 year old male, myasthenic for 29 years, who was treated with pyridostigmine and had a baseline of QMG=6. He returned to the pyridostigmine treatment 72 hours after the last hEN101 dose.

Figure 20:
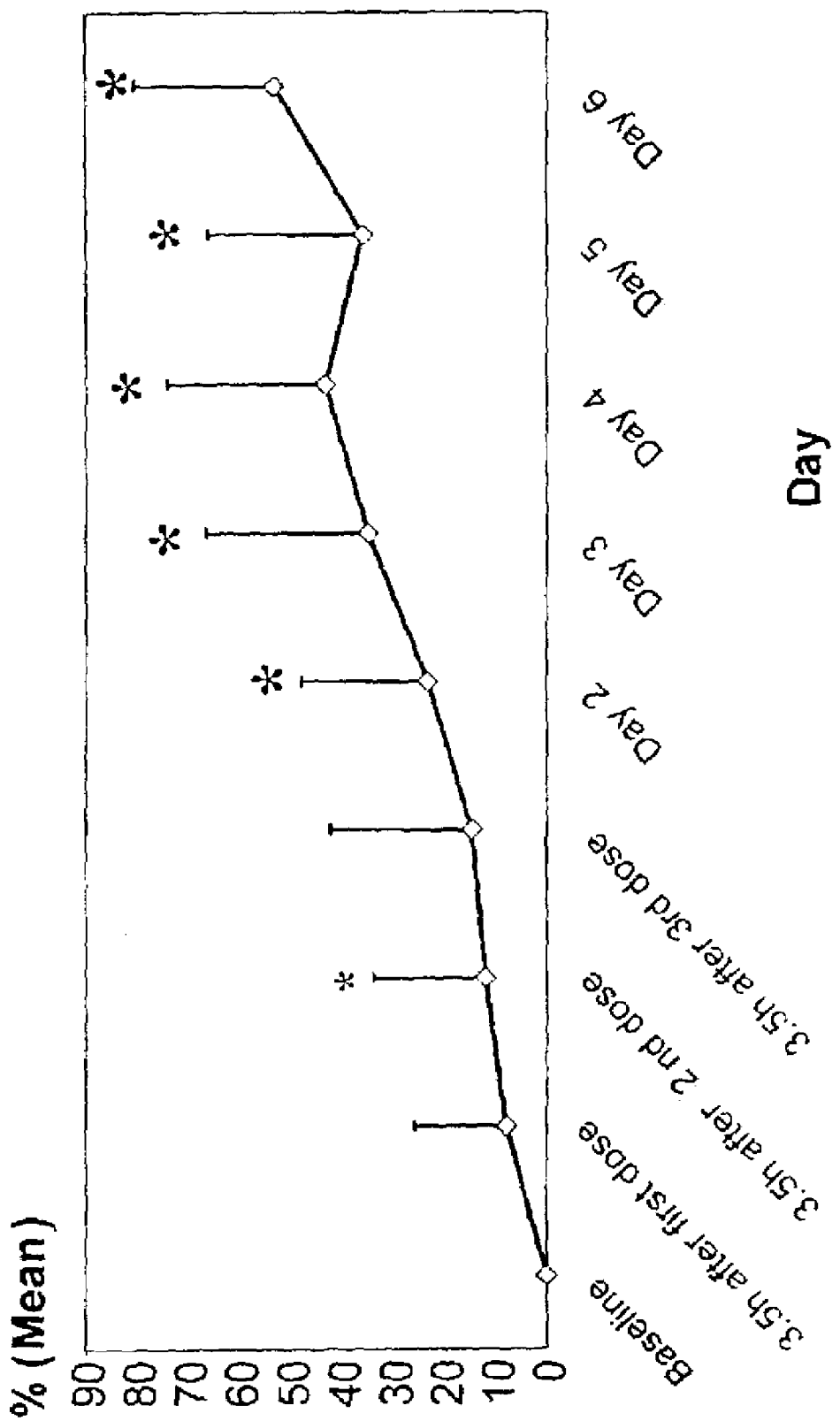

FIG. 20 Improvement in Total QMG Score. Graph shows the mean percentage improvement (plus standard deviation) in total QMG score of all patients, from the baseline value until day 6 of treatment.

Figure 21A:
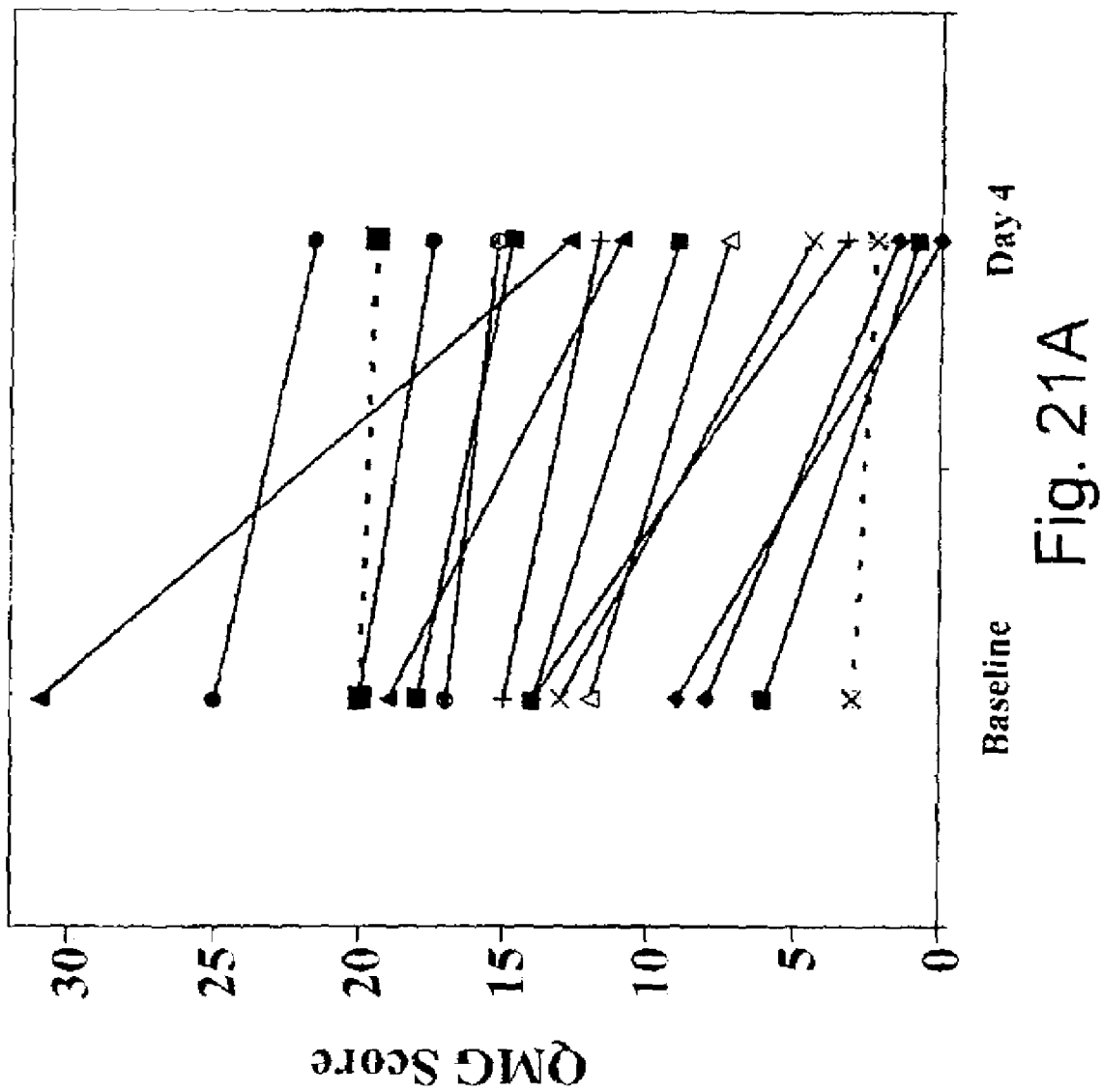
Figure 21B:
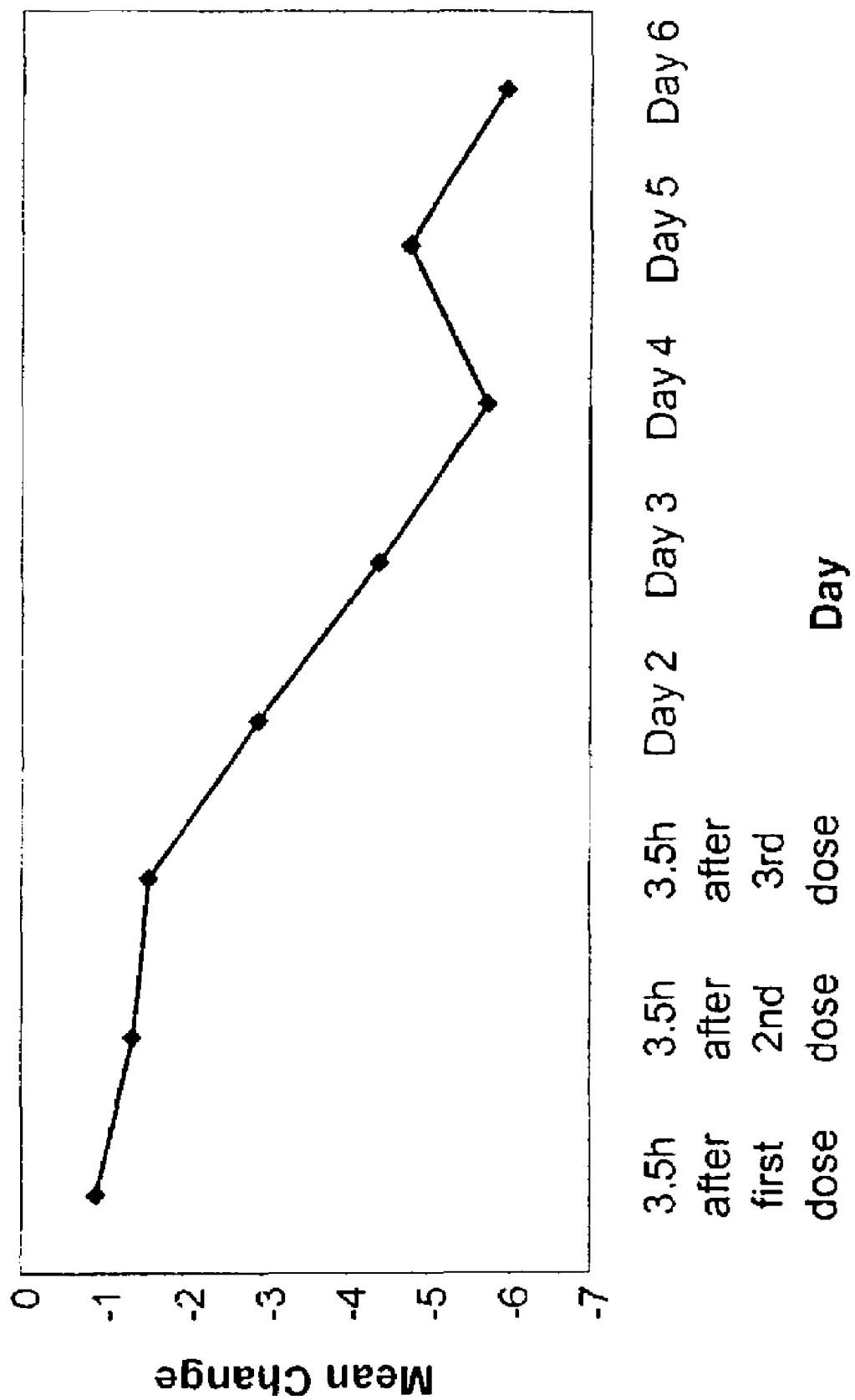

FIG. 21A–B hEN101 improves myasthenic status.

FIG. 21A Graph shows QMG score of all the patients included in the clinical trial.

FIG. 21B Graph shows mean change from baseline in QMG score.

DETAILED DESCRIPTION OF THE INVENTION

For the purposes of clarity, the following abbreviations and terms are defined herein:
AChE: acetylcholinesterase
ACHE-R: acetylcholinesterase, "readthrough" variant or isoform, its mRNA includes pseudo-intron I4
AChE-S: acetylcholinesterase, synaptic variant or isoform
AS-ON: antisense oligonucleotide
BBB: blood-brain barrier
CMAP: compound muscle action potential
CNS: central nervous system
EAMG rat: rats wherein experimental autoimmune myasthenia gravis has been induced
EN101: may also be referred as AS3; antisense oligonucleotide targeted against human, rat or mouse (hEN101, rEN101 or mEN101, respectively) AChE mRNA
EN102: may also be referred as AS1, antisense oligonucleotide targeted against AChE mRNA, at a different region than EN101
MG: myasthenia gravis, a neuromuscular junction disease
i.v.: intravenous
o.g.: oral gavage
p.o.: per os
Antisense oligonucleotide: A nucleotide comprising essentially a reverse complementary sequence to a sequence of AChE mRNA. The nucleotide is preferably an oligodeoxynucleotide, but also ribonucleotides or nucleotide analogues, or mixtures thereof, are contemplated by the invention. The antisense oligonucleotide may be modified in order to enhance the nuclease resistance thereof, to improve its membrane crossing capability, or both. The antisense oligonucleotide may be linear, or may comprise a secondary structure. It may also comprise enzymatic activity, such as ribozyme activity.

Progressive neuromuscular disorder: A disorder or condition associated with excess AChE mRNA or protein production, characterized by changes in the morphology of the NMJ and impairment in neuromuscular transmission. The neuromuscular disorder may involve muscle distortion, muscle re-innervation or NMJ abnormalities. More preferably, the progressive neuromuscular disorder is myasthenia gravis, muscular dystrophy, multiple sclerosis, amyotrophic lateral sclerosis, post-traumatic stress disorder (PTSD), or dystonia.

The present invention relates to a novel antisense oligodeoxynucleotide substantially as denoted by SEQ ID NO:1, also designated herein as hEN101.

In addition to the part of the sequence which is complementary to AChE sequence, the antisense oligonucleotide of the invention may also comprise RNA sequences with enzymatic nucleolytic activity, or may be linked to such sequences. Preferred nucleolytic sequences are ribozyme sequences, which were shown to specifically interact with mRNA transcripts. They are ribonucleic acid sequences, including RNase active sites flanked by antisense oligonucleotides [Haseloff and Gerlach (1988) Nature 3, p. 585, Sarver et al. (1990) Science 247, p. 1222]. Preferred ribozymes are hammerhead ribozymes [Conaty et al. (1999) Nucleic Acids Res. 27, 2400–2407; and Xu et al. (1999) Endocrinology, 140, 2134–44]. Another preferred ribozyme is the hairpin ribozyme structure, e.g., as derived from tobacco ringspot virus satellite RNA [see Perez-Ruiz (1999) Antisense Nucleic Acid Drug Dev., 9, 33–42].

The novel antisense oligodeoxynucleotide of the invention corresponds to the reverse complement of human AChE mRNA sequence, from nucleotide 795-5' to nucleotide 3'-814 (FIG. 1). Prior work by the present inventors has demonstrated the usefulness of antisense oligonucleotide in suppressing AChE production and in the treatment of memory deficiency. In said prior work, a number of AChE antisense oligonucleotides have been disclosed. Said prior work further discloses desirable features of such antisense oligonucleotides and possible modifications thereof, such as nuclease resistance, modifications to enhance membrane transport of oligonucleotides, and the like. Said prior work, e.g. WO 98/26026, is therefore incorporated herein in its entirety by reference. In another publication, the present inventors describe the role of antisense oligonucleotides in the treatment of a variety of neurodegenerative diseases [Seidman, S. et al., Antisense Res. Nucl. Acids Drug Devel. 9, 333–340 (1999)].

The antisense oligodeoxynucleotide of the invention is preferably nuclease resistant. There are a number of modifications that impart nuclease resistance to a given oligonucleotide. Reference is made to WO 98/26062, which publication discloses that oligonucleotides may be made nuclease resistant e.g., by replacing phosphodiester internucleotide bonds with phosphorothioate bonds, replacing the 2'-hydroxy group of one or more nucleotides by 2'-O-methyl groups, or adding a nucleotide sequence capable of forming a loop structure under physiological conditions to the 3' end of the antisense oligonucleotide sequence. An example for a loop forming structure is the sequence 5' CGCGAAGCG (SEQ ID NO:2), which may be added to the 3' end of a given antisense oligonucleotide to impart nuclease resistance thereon.

The cells on which the antisense oligonucleotide of the invention exerts its effects are preferably muscle cells and cells of the NMJ, including the nerve axons and endplate structures.

Using the antisense oligonucleotides according to the invention, it is expected that AChE-R amount and AChE-R mRNA levels are reduced in central nervous system neurons by at least about 30%, preferably by at least about 40%, and more preferably by at least about 50%, within 24 hr of the treatment, and by about 80% under repeated treatment. This reduction was shown by fluorescent in situ hybridization (FISH) and immune labeling and its effectiveness was confirmed by electrophysiology and tread mill tests. It exceeded by far all previous reports of AS-ON destruction of AChE-R mRNA in other cells and tissues.

In yet another embodiment of the invention, the preferred treatment window of candidate oligonucleotides is evaluated by FISH. The technique of in situ hybridization is well known to the man of skill in the art, and is described e.g., In situ Hybridization, Wilkinson, D. G. (Ed.) ISBN: 0199633274; In situ Hybridization for the Brain, Wisden W., Morris B. J. (Eds.), ISBN: 0127599207, PCR in situ Hybridization: A Practical Approach (Practical Approach Series 186), Herrington C. S., John O'Leary J., (Eds.) ISBN: 019963632X. Detailed protocols relating to in situ hybridization using non-radioactively labeled probes are available from Microsynth GmbH (Balgach, Switzerland).

Labeled AChE-R cRNA sequences may be used as probes for in situ hybridization. The ACHE cRNA probe preferably comprises I4 pseudo-intron sequences.

In a preferred embodiment of the invention, the AChE mRNA determination is carried out by using in situ RT-PCR, which technique is described, e.g., in the above-mentioned references, see also PCR in situ hybridization: Protocols and Applications, 3rd ed., by Nuovo, G. J. Lippincott, Raven Press, New York (1996).

Phosphorothioate-modified oligonucleotides are generally regarded as safe and free of side effects. Peng et al. teach that undesired in vivo side effects of phosphorothioate antisense oligonucleotides may be reduced when using a mixed phosphodiester-phosphorothioate backbone. The antisense oligonucleotides of the present invention have been found to be effective as partially phosphorothioates and yet more effective as partially 2'-O-methyl protected oligonucleotides. WO 98/26062 teaches that AChE antisense oligonucleotides containing three phosphorothioate bonds out of about twenty internucleotide bonds are generally safe to use in concentrations of between about 1 and 10 µM. However, for long-term applications, oligonucleotides that do not release toxic groups when degraded may be preferred. These include 2'-O-methyl protected oligonucleotides, but not phosphorothioate oligonucleotides. A further advantage of 2'-O-methyl protection over phosphorothioate protection is the reduced amount of oligonucleotide that is required for AChE suppression. This difference is thought to be related to the improved stability of the duplexes obtained when the 2'-O-methyl protected oligonucleotides are used [Lesnik, E. A. & Freier, S. M., *Biochemistry* 37, 6991–7, (1998)]. An alternative explanation for the greater potency of the 2'-O-methyl oligonucleotides is that this modification may facilitate penetration of the oligonucleotide chain through the cell membrane. A further advantage of 2'-O-methyl protection is the better protection against nuclease-mediated degradation that it confers, thus extending the useful life time of antisense oligonucleotides protected in this way.

In accordance with the invention, the dosage of the antisense oligodeoxynucleotide is about 0.001 to 50 µg oligonucleotide per gram of body weight of the treated animal. Preferably, the dosage is about 0.01 to about 5.0 µg/g. More preferably, the dosage is between about 0.05 to about 0.7 µg/g. Thus, the optimal dose range is between 50–500 µg/kg of body weight of the treated subject, for rats, monkeys and also humans.

The antisense oligonucleotide of the invention is provided for use in the treatment of a disorder that involves excessive AChE mRNA production.

The disorder is preferably a disorder involving functional and morphological changes in the NMJ.

The progressive neuromuscular disorder preferably involves overexpression of AChE-R mRNA.

More preferably, the disorder is selected from, but not limited to, multiple sclerosis, PTSD, *myasthenia gravis,* muscular dystrophy, amyotrophic lateral sclerosis, dystonia, muscle distortion, muscle re-innervation or excessive muscle innervation.

The excessive muscle innervation is selected preferably from, but not limited to, excessive innervation after trauma, preferably after amputation.

In one aspect, the invention relates to a pharmaceutical composition for the treatment and/or prevention of a progressive neuromuscular disorder, for improving stamina in physical exercise and/or for use in decreasing chronic muscle fatigue, comprising as active ingredient the synthetic antisense oligodeoxynucleotide hEN101, as denoted by SEQ ID NO:1, and optionally further comprising additional therapeutic agents and/or pharmaceutically acceptable carriers, excipients and/or diluents. Preferably, said pharmaceutical composition is for the treatment and/or prevention of myasthenia gravis.

The progressive neuromuscular disorder to be treated and/or prevented by the pharmaceutical composition of the invention is associated with an excess of AChE or protein. Usually, said excessive AChE will be the AChE-R variant or isoform.

In addition, said progressive neuromuscular disorder to be treated and/or prevented by the pharmaceutical composition of the invention is associated with impairment of the cholinergic transmission. Said disorder may involve muscle distortion, muscle re-innervation, or neuromuscular junction (NMJ) abnormalities.

The pharmaceutical composition of the invention is for use in the treatment and/or prevention of a disorder such as myasthenia gravis (MG), Eaton-Lambert disease, muscular dystrophy, amyotrophic lateral sclerosis (ALS), post-traumatic stress disorder (PTSD), multiple sclerosis (MS), dystonia, post-stroke sclerosis, post-injury muscle damage, excessive re-innervation, post-surgery paralysis of unknown origin and post-exposure to AChE inhibitors.

In one embodiment, the pharmaceutical composition of the invention is for daily use by a patient in need of such treatment, at a dosage of active ingredient between about 0.001 µg/g and about 50 µg/g. Preferably, the treatment and/or prevention comprises administering a dosage of active ingredient of about 0.01 to about 5.0 µg/g. Most preferably, said dosage of active ingredient is of between about 0.05 to about 0.70 µg/g, and even most preferably, the dosage is from 0.15 to 0.50 µg/g of body weight of the patient.

As may be seen in Example 11 and FIGS. 18–21, treatment of MG patients with hEN101 resulted in significant improvement of the clinical symptoms. As an example of such improvements, FIG. 18 shows how patients were capable of better opening their eyes (lifting their eye lids), and their QMG scores improved significantly (FIG. 19–21). Thus, hEN101 has proved to be effective in reversing the symptoms in human MG patients.

The pharmaceutical composition of the invention may optionally comprise at least one additional active agent. Said active agent may be, for example, AChE inhibitors used for the treatment of neuromuscular disorders.

In a further aspect, the invention relates to a pharmaceutical composition comprising an antisense oligodeoxynucleotide as denoted by SEQ ID NO:1, for facilitating passage of compounds through the BBB, optionally further comprising additional pharmaceutically active agent and/or pharmaceutically acceptable adjuvant, carrier or diluent. The additional pharmaceutically active agent is a compound to be transported through the BBB. These pharmaceutical compositions of the invention may be used for treatment of disorders associated with the central nervous system, particularly such disorders that require administration of an active agent into the CNS, for example, for the treatment of brain tumors. Conventional chemotherapeutic agents do not pass the BBB, and are therefore ineffective [de Angelis, L. M., *N. Engl. J Med.* 433, 114–123 (2001)]. As the antisense oligonucleotide of the invention has been shown to penetrate the BBB, brain tumors could be treated by injection or oral administration of the antisense oligonucleotide of the invention, preventing or reducing the need for methods requiring invasion of the CNS. Antisense oligonucleotides can be made tumor-specific [Ratajczak M. Z. et al. *Proc. Natl. Acad. Sci. USA* 89, 11823–11827 (1992)]; therefore should they be found to pass the BBB, they may be both specific and effective. Thus, the additional pharmaceutical agents comprised in these compositions of the invention may be, for example carcinostatic and metastatic drugs.

A number of compounds are needed for the diagnostic or treatment of conditions affecting the central nervous system, wherein the BBB would normally impede their delivery. These conditions can include any disease or pathology, which include but are not limited to infections, neurochemical disorders, brain tumors and gliomas, demyelination, other neuropathies, encephlopathies, coma, ischemia, hypoxia, epilepsy, dementias, cognitive disorders, neuropsychiatric disorders (as for example depression, anxiety, schizofrenia and the like), as well as genetic disorders. Thus, said compounds or additional pharmaceutically active agent to be transported across the BBB may be, for example, contrast agents (dyes) used for central nervous system imaging, drugs such as antibiotics or chemotherapeutics, gene therapy vectors, or even agents that function to block the effects of abused drugs. The administration and dosage of these compounds shall be according to what is known in medical practice, which generally should take into account the clinical condition of the patient in need of such treatment, as well as said patient's age, sex, body weight and other factors known to be important in the medical practice. The site and method of administration should also be chosen accordingly. The pharmaceutically effective amount for purposes herein is thus determined by such considerations as are known in the art. The compound can be administered in several ways as described for the delivery of the composition (see below).

The compound to be transported through the BBB may be administered simultaneously with the composition of the invention or can be administered at some point during the biologically effective period of the action of the composition. In other words, the composition of the invention facilitates the disruption of the BBB, i.e. it opens the BBB, for a period of time depending on its dose and the compound can then be administered during this "open" period.

In order to be effective, the antisense oligonucleotide of the invention, also when comprised in a pharmaceutical composition of the invention, must travel across cell membranes. In general, antisense oligonucleotides have the ability to cross cell membranes, apparently by a saturable uptake mechanism linked to specific receptors. As antisense oligonucleotides are single-stranded molecules, they are to a degree hydrophobic, which enhances passive diffusion through membranes. Modifications may be introduced to an antisense oligonucleotide to improve its ability to cross membranes. For instance, the oligonucleotide molecule may be linked to a group comprising optionally partially unsaturated aliphatic hydrocarbon chain and one or more polar or charged groups such as carboxylic acid groups, ester groups, and alcohol groups. Alternatively, oligonucleotides may be linked to peptide structures, which are preferably membranotropic peptides. Such modified oligonucleotides penetrate membranes more easily, which is critical for their function and may therefore significantly enhance their activity. Palmityl-linked oligonucleotides have been described by Gerster et al. [*Anal. Biochem.* 262, 177–84 (1998)]. Geraniol-linked oligonucleotides have been described by Shoji et al. [*J. Drug Target* 5, 261–73 (1998)]. Oligonucleotides linked to peptides, e.g., membranotropic peptides, and their preparation have been described by Soukchareun et al. [*Bioconjug. Chem.* 9, 466–75 (1998)]. Modifications of antisense molecules or other drugs that target the molecule to certain cells and enhance uptake of the oligonucleotide by said cells are described by Wang, J. [*Controlled Release* 53, 39–48 (1998)].

Any of the compositions of the invention are for use by injection, topical administration or oral uptake. Preferred uses of the pharmaceutical compositions of the invention by injection are subcutaneous injection, intraperitoneal injection, and intramuscular injection. As shown in the following Examples, oral administration proved very effective, it is much easier to prescribe and meet patient compliance, and it involves more easy handling.

The compositions of the present invention suitable for oral administration may be presented as discrete units such as capsules, sachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary or paste. A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

The pharmaceutical compositions of the invention generally comprise a buffering agent, an agent which adjusts the osmolarity thereof, and optionally, one or more carriers, excipients and/or additives as known in the art, e.g., for the purposes of adding flavors, colors, lubrication, or the like to the pharmaceutical composition. A preferred buffering agent is phosphate-buffered saline solution (PBS), which solution is also adjusted for osmolarity.

Carriers may include starch and derivatives thereof, cellulose and derivatives thereof, e.g., microcrystalline cellulose, xantham gum, and the like. Lubricants may include hydrogenated castor oil and the like.

A preferred pharmaceutical formulation is one lacking a carrier. Such formulations are preferably used for administration by injection, including intravenous injection.

The preparation of pharmaceutical compositions is well known in the art and has been described in many articles and textbooks, see e.g., Remington's Pharmaceutical Sciences, Gennaro A. R. ed., Mack Publishing Co., Easton, Pa., 1990, and especially pp. 1521–1712 therein.

Additives may also be designed to enhance uptake of the antisense oligonucleotide across cell membranes. Such agents are generally agents that will enhance cellular uptake of double-stranded DNA molecules. For instance, certain lipid molecules have been developed for this purpose, including the transfection reagents DOTAP (Roche Diagnostics), Lipofectin, Lipofectam, and Transfectam, which are available commercially. For a comparison of various of these reagents in enhancing antisense oligonucleotide uptake see e.g., Quattrone et al. [*Biochemica* 1, 25, (1995)] and Capaccioli et al. [*Biochem. Biophys. Res. Comm.* 197, 818 (1993). The antisense oligonucleotide of the invention may also be enclosed within liposomes. The preparation and use of liposomes, e.g., using the above mentioned transfection reagents, is well known in the art. Other methods of obtaining liposomes include the use of Sendai virus or of other viruses. Examples of publications disclosing oligonucleotide transfer into cells using the liposome technique are e.g., Meyer et al. [*J. Biol. Chem.* 273, 15621–7 (1998)], Kita and Saito [*Int. J. Cancer* 80, 553–8 (1999)], Nakamura et al. [*Gene Ther.* 5, 1455–61 (1998)] Abe et al. [*Antivir. Chem. Chemother.* 9, 253–62 (1998)], Soni et al. [*Hepatology*, 28, 1402–10 (1998)], Bai et al. [*Ann. Thorac. Surg.* 66, 814–9 (1998) and see also discussion in the same journal p. 819–20], Bochot et al. [*Pharm. Res.* 15, 1364–9 (1998)], Noguchi et al. [*FEBS Lett.* 433, 169–73 (1998)], Yang et al. [*Circ. Res.* 83, 552–9 (1998)], Kanamaru et al. [*J. Drug Target.* 5, 235–46 (1998)] and references therein. The use of Lipofectin in liposome-mediated oligonucleotide uptake is described in Sugawa et al. [*J. Neurooncol.* 39, 237–44 (1998)]. The use of fusogenic cationic-lipid-reconstituted influenza virus envelopes (cationic virosomes) is described in Waelti et al. [*Int. J. Cancer*, 77, 728–33 (1998)].

The above-mentioned cationic or nonionic lipid agents not only serve to enhance uptake of oligonucleotides into cells, but also improve the stability of oligonucleotides that have been taken up by the cell.

The invention also relates to a method for the treatment or prevention of a progressive neuromuscular disorder or other disease involving excessive production of AChE-R mRNA, comprising administering the oligodeoxynucleotide of the invention or a pharmaceutical composition of the invention or of any of the preferred embodiments thereof, to a patient in need thereof.

Lastly, the invention relates to a method of administering to a patient in need of such treatment a therapeutic agent for treatment of a disorder or disease of the CNS, comprising the steps of administering to said patient the antisense oligodeoxynucleotide of the invention and said therapeutic agent. The administration of the therapeutic agent may be simultaneous with the administration of that of the antisense oligodeoxynucleotide of the invention, or preceding or following the same. Rupture of the BBB by the antisense oligodeoxynucleotide of the invention will facilitate the passage of the therapeutic agent across the BBB and into the CNS, where its effect is required.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Animals:

Rats: EAMG was induced in female Lewis rats (120–150 g) purchased from the Jackson Laboratory (Bar Harbor, Me.), and housed in the Animal Facility at the Hebrew University Faculty of Medicine, in accordance with NIH guidelines. Control FVB/N mice were subjected to confined swim stress as described [Kaufer et al., 1998 id ibid.]. Transgenic FVB/N mice overexpressing AChE-R were as detailed [Sternfeld et al. (2000) *Proc. Natl.Acad. Sci. USA* 97, 8647–8652].

Monkeys: Purpose-bred female and male 15 month-old Cynomolgus monkeys were used.

Oligonucleotides: HPLC-purified, GLP grade oligonucleotides (purity >90% as verified by capillary electrophoresis) were purchased from Hybridon, Inc. (Worchester, USA). Lyophilized oligonucleotides were resuspended in sterile double distilled water (24 mg/ml), and stored at −20° C. The oligonucleotides were prepared with phosphodiester linkages at all but the three terminal 3' positions at which 2'-O-methyl ribonucleotide substitutions were made. The primary sequences used in this study were:

hEN101
5'-CTGCCACGTTCTCCTGCACC-3'
(human AS3, SEQ ID NO:1)
2'-O-methylated hEN101 (methylated nucleotides
marked with *)
5'-CTGCCACGTTCTCCTGCA*C*C*-3' mEN101
5'-CTGCAATATTTTCTTGCACC-3'
(mouse AS3, SEQ ID NO:3) [Grifman, M., and
Soreq, H. (1997) Antisense Nucleic Acid
Drug Dev 7, 351-9]

rEN101
5'-CTGCGATATTTTCTTGTACC-3'
(rat AS3, SEQ ID NO:4) [WO98/26062]

rEN102
5'-GGGAGAGGAGGAGGAAGAGG-3'
(SEQ ID NO:5) [WO98/26062]

r-invEN102
5'-GGAGAAGGAGGAGGAGAGGG-3'
(SEQ ID NO:6) [Meshorer, E. et al. (2002) id ibid]

Stability of hEN101: hEN101 was found to be stable (>90% of original concentration) after storage for 2 h in human plasma with EDTA at room temperature, following three freeze/thawing cycles, or after 1 month at −20° C. Exposure at room temperature to Li-heparin-treated blood caused a decay of hEN101 with a half-life in the order of 30 min.

Antibodies: Rabbit polyclonal antibodies against the C-terminal AChE-R were prepared and purified as described [Sternfeld et al. (2000) ibid.]. Goat polyclonal anti-AChR (C-20, S.C.-1448) antibodies were from Santa Cruz, (Santa Cruz, Calif.).

Induction of EAMG: Torpedo acetylcholine receptor (T-AChR) was purified from *T. californica* electroplax by affinity chromatography on neurotoxin-Sepharose resin, as previously described [Boneva, N. et al. (2000) *Muscle & Nerve* 23, 1204–8]. Rats were immunized with 40 μg of purified T-AChR emulsified in complete Freund's adjuvant supplemented with 1 mg of *M. tuberculosis* H37Ra (Difco, Detroit Mich.). The animals were injected subcutaneously in the hind footpads and a booster injection of the same amount was given after 30 days. A third injection was administered to animals that did not develop EAMG after the second injection. Animals were weighed and inspected weekly during the first month and daily after the booster immunization, for evaluation of muscle weakness. The clinical status of the rats was graded according to: 0—Without definite weakness (treadmill running time, 23±3 min); mild (1)—weight loss >3% during a week, >10 min. running time on treadmill; moderate (2)—moderate weakness accompanied by weak grip or cry with fatigue, weight loss of 5–10%, 3–5 min. running on treadmill; moderate-severe (3)—moderate to severe weakness, hunched back posture at rest, head down and forelimb digit flexed, tremulous ambulation, 10% body weight loss, 1–2 min. run on treadmill); severe (4)—severe general weakness, no cry or grip, treadmill running time <1 min, weight loss >10%; (5)—death.

Anti-AChR antibody determination: Serum was assayed by direct radioimmunoassay, using $^{125}$I-α bungarotoxin (BgT) bound to T-AChR and to rat (R) AChR [Boneva et al. (2000) id ibid]. All the EAMG rats displayed high anti-T-AChR or anti-R-AChR titers, with serum mean±standard error (SE) values of 82.1±16.0 nM for anti-T-AChR antibodies and 19.9±1.8 nM for anti-R-AChR. Human serum was tested for the level of anti-AChR antibodies as previously described [Drachman, D. B. (1994) *N Engl J Med* 330, 1797–810].

Quantification of nAChR: AChR concentration in the gastrocnemius and tibialis muscles was determined using $^{125}$I-α-BgT binding followed by precipitation by saturated ammonium sulfate as described previously [Boneva et al. (2000) id ibid].

Immunocytochemistry: Muscle sections were deparaffinized with xylene and were re-hydrated in graded ethanol solutions (100%, 90%, 70%) and PBS. Heat-induced antigen retrieval was performed by microwave treatment (850 W for rapid boil following 10 min in reduced intensity) in 500 ml of 0.01M citrate buffer pH 6.0. Slides were cooled to room temperature and rinsed in double distilled water. Non-specific binding was blocked by 4% normal donkey serum in PBS with 0.3% Triton X-100 and 0.05% Tween 20 (1 hr at room temperature). Biotinylated primary antibody was diluted (1:100 and 1:30 for rabbit anti-AChE-R [Sternfeld et al. (2000) id ibid] and goat anti-nAChR, respectively) in the same buffer and slides were incubated 1 hr at room temperature following overnight incubation at 4° C. Sections were rinsed and incubated with alkaline phosphatase-conjugated secondary antibody, diluted in the same blocking buffer 1 hr at room temperature and then overnight at 4° C. Detection was with the alkaline phosphatase substrate Fast Red (Roche Diagnostics, Mannheim, Germany). Slides were simultaneously transferred to a stop solution (25 mM EDTA, 0.05% Triton X-100, 1 mM levamisole in PBS, pH 7.2), rinsed in PBS and cover-slipped with Immunomount (Shandon).

For spinal cord sections, primary mouse anti-SC35 antibody was diluted (1:100) in the same buffer as the previous primary antibodies, and slides were incubated 1 h at room temperature following overnight incubation at 4° C. Sections were rinsed and incubated with peroxidase conjugated goat anti-mouse secondary antibody, diluted in the same blocking buffer, for 1 h at room temperature and then overnight at 4° C. Detection was performed with DAB substrate (Sigma). Slides were cover-slipped with Immunomount (Shandon, Pittsburgh, Pa.).

Electromyography: Rats were anesthetized by i.p. injection of 2.5 mg/Kg pentobarbital, immobilized, and subjected to repetitive sciatic nerve stimulation, using a pair of concentric needle electrodes at 3 Hz. Baseline compound muscle action potential (CMAP) was recorded by a concentric needle electrode placed in the gastrocnemius muscle, following a train of repetitive nerve stimulations at supramaximal intensity. Decrease (percent) in the amplitude of the fifth vs. the first muscle action potential was determined in two sets of repetitive stimulations for each animal. A reduction of 10% or more was considered indicative of neuromuscular transmission dysfunction.

Drug administration: Intravenous injections and blood sampling for anti-AChR antibodies testing were via the right jugular vein under anesthesia. For oral administration, a special needle for oral gavage feeding was used, which is curved with a ball end (Stoelting, Wood Dale Ill.). Mestinon® was administered in a dose of 1 mg/kg/day, and purchased from Hoffmann La-Roche, Basel, Switzerland.

Exercise training on treadmill: To establish a clinical measure of neuromuscular performance in EAMG rats, a treadmill assay was performed. Animals were placed on an electrically powered treadmill [Moran et al. (1996) *J Therm Biol* 21, 171–181] at 25 m/min (a physical effort of moderate intensity) until visibly fatigued. The amount of time the rats were able to run was recorded before and after anti-sense or Mestinon® treatment.

In situ hybridization: Tissues were fixed in 4% paraformaldehyde and cut into 7 μm paraffin embedded sections.

Spinal cord sections were deparaffinized, rehydrated using serial ethanol dilutions and permeabilized with proteinase K (10 μg/ml at room temp.). Slides were exposed to 5' biotinylated, fully 2'-oxymethylated AChE-R or AChE-S- specific 50-mer cRNA probes complementary to human ACHE pseudo-intron 4 or exon 6, respectively [Grisaru et al. (2001) id ibid.]. Hybridization was performed overnight at 52° C. in hybridization mixture containing 10 μg/ml probe, 50 μg/ml yeast tRNA, 50 μg/ml heparin and 50% formamide in 375 mM Na chloride, 37.5 mM Na citrate, pH 4.5. For monkey sections, the probe was constructed according to the human AChE-R sequence; for rat sections, according to the mouse sequence. Slides were washed to remove non-hybridized probe, blocked with 1% skim milk containing 0.01% Tween-20 and 2 mM levamisole, an alkaline phosphatase inhibitor used to suppress non-specific staining and incubate with streptavidin-alkaline phosphatase (Amersham Pharmacia). Fast Red™ substrate (Roche Diagnostics) was used for detection. DAPI staining (Sigma Chemical Co., St. Louis, Mo., USA) served to visualize nuclei. Microscope images were analyzed with Image Pro Plus 4.0 (Media Cybernetics) software.

Serum analyses: Blood samples drawn from EAMG rats and MG patients were subjected to non-denaturing gel electrophoresis as described [Kaufer et al. (1998) id ibid], as well as to catalytic activity measurements of AChE [Shapira et al. (2000) id ibid]. Iso-OMPA (tetraisopropylpyrophosphoramide, $5 \times 10^{-5}$ μM), was used to block butyrylcholinesterase activity in the serum samples. For activity staining on polyacrylamide gels [Kaufer et al. (1998) id ibid] we used 510-6 M iso-OMPA.

Protocol for Phase Ib Clinical Trial of MG patients using hEN101: Patients were hospitalized and pyridostigmine was discontinued for 12–18 hours before EN101 testing. Assessment of MG status was performed first at entry, then after pyridostigmine stoppage, and regularly after EN101 treatment using a Quantitative MG (QMG) score. Escalating oral doses of EN101 (10–150 μg/kg) were given in the first day (day 1), followed by a daily dose of 500 μg/kg for 3 days (days 2–4). Days 5 and 6 were washout period without pyridostigmine, and restitution of pyridostigmine occurred when it became necessary. Patients were monitored for 1 month thereafter, with three visits as out-patients.

The following parameters were used as inclusion criteria:
Class II and above, according to MGFA classification (myasthenia gravis standard clinical classification of the disease severity score);
Age 18–70;
Seropositive for AChR antibodies;
Patients under pyridostigmine (180 mg/day) treatment without concomitant immunosuppressants;
Stable for 3 months, with no PE (plasma exchange) for 6 months;
No other major or active diseases.

Evaluation of the MG status of each patient was based on the following parameters:
(a) QMG scoring (maximum value of 9), based on the measurements of:
Fatigue in each limb (4);
Fatigue of the neck (1);
Swallowing rate (1);
Power in the hands (2);
Respirometry (1).
These measurements were taken daily, 4 times per day, and averaged for days 2–6.
(b) Patient's subjective report;
(c) Vital signs, clinical chemistry, hematology, urinalysis, ECG and physical examination, recorded daily.

EXAMPLE 1

AChE-R Accumulate in Blood and Muscle of EAMG Rats

Figure 7:
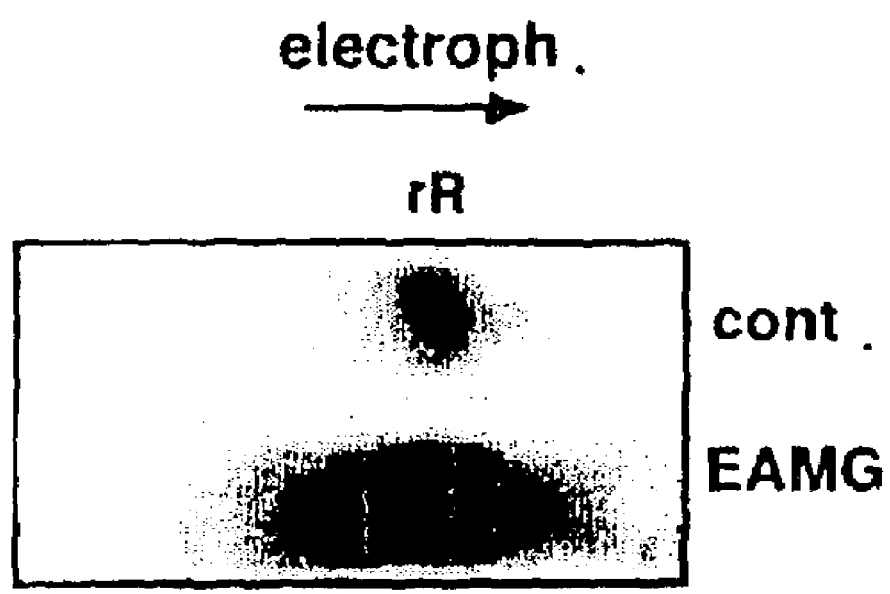
FIG. 7 Immunoreactive AChE-R in EAMG rats.

As previously shown by the inventors, the AChE-R variant migrates on non-denaturing polyacrylamide gels faster than the tetrameric synaptic enzyme, AChE-S [Kaufer et al. (1998) id ibid.], and it is present in the serum of MG patients [WO01/36627]. Similarly, immunoblot analysis confirmed that in EAMG rats, as compared with healthy rats, there was a massive increase in serum AChE-R (FIG. 7).

Expression of alternative AChE variants (FIG. 8A), as well as of the nicotinic acetylcholine receptor (nAChR), was tested in control and EAMG rats. Depletion of nAChR in muscle sections from EAMG rats was detected, as evidenced by a quantitative immunoassay using antibodies against nAChR (FIG. 8B, 1 and 2). The immunostaining showed that muscle nAChR was reduced by 48±7% from normal values in 10 mildly affected animals (disease grade 1–2, see Experimental Procedures) and by 75±5% in 10 severely affected rats (grade 4) compared to controls (FIG. 8B, 1 and 2), attesting to the myasthenic nature of this animal model. Immunohistochemical staining with a polyclonal antiserum that selectively detects AChE-R [Sternfeld et al. (2000) id ibid] revealed positive signals in some, but not all muscle fibers of control rats. Similar patterns appeared under treatment with the inert, inversely oriented oligonucleotide r-invEN102 (see FIG. 8B, 3). In EAMG rats (FIG. 8B, 4), staining of AChE-R showed it as more generally distributed, with the dispersed cytoplasmic localization that is characteristic of this isoform [Soreq, H., and Seidman, S. (2001) *Reviews Neuroscience* 2, 294–302], contrasting with the sub-synaptic cluster distribution of the synaptic variant [Rossi, S. G. and Rotundo, R. L. (1993) *J Biol Chem* 268, 19152–9]. Both the level of expression and the cellular distribution of muscle AChE-S were similar in EAMG and healthy, untreated and r-invEN102-treated rats.

In situ hybridization using variant-selective probes showed that AChE-S mRNA was sub-synaptically located in muscles from both untreated and r-invEN102-treated, healthy and EAMG rats (FIG. 8B, 5 and 6). In contrast, healthy rats displayed weaker and diffuse labeling of the AChE-R mRNA transcript, whereas a more pronounced punctuate labeling of AChE-R mRNA appeared in triceps muscles of EAMG rats, unaffected by r-invEN102 treatment (FIG. 8B, 7 and 8). This accumulation in regions rich in densely clustered nuclei was consistent with previous observations of sub-synaptic regions [Rossi and Rotundo (1993) id ibid]. These data indicate a selective over-expression of AChE-R in muscles of EAMG rats and strengthened the idea of a role for this enzyme variant in MG pathophysiology.

EXAMPLE 2

AChE-R and AChE-R mRNA Levels in Muscle Respond to rEN101

The soluble and secretory nature of AChE-R predicted that it would degrade acetylcholine before it reaches the post-synaptic membrane, limiting receptor activation. To test this hypothesis, rEN101 antisense oligonucleotide was used, which is capable of selective suppression of AChE-R production [Galyam, N. et al. (2001) *Antisense Nucl Acid Drug Dev* 11, 51–57]. AChE-R suppression was tested in healthy and EAMG rats with reduced muscle nAChR levels (FIG. 8B, 1 and 2) 24 h after a single i.v. injection of 250 g/Kg rEN101. Immunohistochemical staining demonstrated that AChE-R, but not AChE-S, was significantly reduced in muscles from both healthy and EAMG rats (FIG. 8C, 3 and 4 and data not shown). Receptor labeling patterns remained high in healthy rats and low in EAMG animals, similar to those of untreated animals and animals treated with r-invEN102 (compare FIG. 8B, 1 and 2 to FIG. 8C, 1 and 2). In situ hybridization indicated that AChE-S mRNA labeling, limited to the sites of subsynaptic clusters of nuclei, was only nominally affected by rEN101, suggesting that neuromuscular transmission would be unaffected by this treatment AChE-R production [Lev-Lehman et al. (2000) id ibid]. Therefore, retrieval of stable CMAP in rEN101-teated EAMG rats may attest to the causal role of AChE-R in the neuromuscular malfunctioning that is characteristic of the myasthenic phenotype. To test this concept, rEN101 was injected i.v. at doses ranging from 10–500 µg/Kg (2 to 20 nmol/rat). rEN101 did not affect CMAP in healthy animals, but retrieved stable CMAP ratios within 1 h (FIG. 9B, inset, 9C and Table 1). CMAP normalization was accompanied by increased mobility, upright posture, stronger grip, and reduced tremulousness of ambulation.

TABLE 1

Post-treatment CMAP ratios[a]

| | Oral[b] | | | | | Intravenous[b] | | | |
|---|---|---|---|---|---|---|---|---|---|
| Phenotype Treatment | Naive EN101 | EAMG EN101 | EAMG EN102 | EAMG invEN102 | EAMG pyridostigmine | Naive EN101 | EAMG EN101 | EAMG EN102 | EAMG invEN102 |
| 0 h | 1.01 ± 0.01 (4) | 0.84 ± 0.03 (8) | 0.82 ± 0.02 (4) | 0.78 ± 0.06 (4) | 0.90 ± 0.01 (6) | 1.00 ± 0.0 (6) | 0.87 ± 0.01 (6) | 0.85 ± 0.06 (4) | 0.89 ± 0.02 (5) |
| 1 h[c] | 1.0 ± 0.02 (4) | 0.97 ± 0.02 (8) | 0.86 ± 0.04 (3) | 0.86 ± 0.05 (4) | 0.98 ± 0.01 (6) | 0.02 ± 0.01 (7) | 1.00 ± 0.01 (4) | 1.04 ± 0.01 (4) | 0.89 ± 0.03 (5) |
| 5 h | 1.03 ± 0.02 (4) | 0.97 ± 0.03 (7) | 0.96 ± 0.02 (4) | 0.86 ± 0.05 (4) | 0.96 ± 0.02 (6) | 1.00 ± 0.01 (6) | 0.98 ± 0.02 (4) | 0.98 ± 0.03 (4) | 0.89 ± 0.02 (5) |
| 24 h | 1.01 ± 0.00 (7) | 1.01 ± 0.01 (6) | 0.95 ± 0.03 (5) | 0.81 ± 0.08 (4) | 0.87 ± 0.02 (6) | 1.02 ± 0.01 (6) | 1.00 ± 0.00 (4) | 1.00 ± 0.01 (4) | 0.90 ± 0.02 (5) |

[a]CMAP ratios ($5^{th}$ vs. $1^{st}$ amplitude) were determined at the noted times following treatment. The averages ± SEM are presented. Each treatment represents similarly, although not simultaneously treated rats, the numbers of which are shown in parentheses.
[b]Drug doses were 50 µg/Kg for rEN101, rEN102 or r-invEN102 and 1000 µg/Kg for pyridostigmine (Mestinon Bromide), for both administration routes.
[c]Note the apparently delayed effect of orally administered rEN102 as compared to rEN101 or pyridostigmine.

(FIG. 8C, 5 and 6). In contrast, rEN101 reduced AChE-R mRNA labeling almost to the limit of detection in both healthy and myasthenic rats (FIG. 8C, 7 and 8).

EXAMPLE 3

Suppression of AChE-R Restores Normal CMAP in EAMG Rats

Quantification by densitometry of an immunoblot analysis confirmed the increase of serum AChE-R in EAMG and the efficacy of a single i.v. injection of 250 µg/Kg rEN101, but not r-invEN102, in reducing its serum level 24 h later (FIG. 9A). To evaluate the physiological outcome of this suppression, compound muscle action potentials (CMAPs) from the gastrocnemius muscle were recorded. EAMG rats, but never healthy animals, displayed a decline in CMAP during repeated stimulation at 3 Hz. The baseline decline, the percent difference in the heights of the fifth and the first evoked potentials, ranged from 10% to 36% (mean±SEM=13.0±2.5%, FIG. 9B, inset) as compared to 4.0±0.9% among healthy rats. The standard therapy for MG patients is administration of anti-cholinesterases, which elevate ACh levels to a threshold that enables receptor activation. Accordingly, neostigmine bromide (Prostigmine™, 75 µg/kg) was administered via i.p. This rapidly and effectively corrected the CMAP decline in EAMG rats, from 87.6% of the first evoked potential in untreated animals to over 120% of this level (i.e. 107.4%) of the first evoked potential). The effects of the cholinesterase blockade were evident starting 15 min after the injection and lasted 2 h, after which time the CMAP value returned to the baseline (FIG. 9B).

Unlike anticholinesterases, which block all AChE variants, rEN101 was shown to selectively suppress muscle Both the extent and the duration of CMAP correction were dose dependent. For example, 500 µg/Kg conferred 72 h rectification of CMAP up to 125% of baseline, while 50 µg/Kg was effective for only 24 h. rEN102, a 3' protected AS-ON targeting a sequence unique to rAChE-R mRNA (previously referred to as AS1) [Grifman and Soreq (1997) id ibid], induced similar rectification of CMAP decline in EAMG rats, confirming the relevance of AChE-R as a contributing element to this effect. Comparable amounts of r-invEN102, did not improve muscle function, attesting to the sequence specificity of the AS-ON treatment (Table 1). Dose response curves revealed that up to 5 h following an injection, rEN101 produced a saturable response with $IC_{50}$ of <10 µg/Kg. This effect appeared to be superimposed on a longer lasting and less concentration-dependent effect, which showed no saturation in the range studied (FIG. 9D). This phenomenon possibly reflected the altered muscle and/or neuromuscular junction properties under the stable CMAP retrieval afforded by rEN101.

EXAMPLE 4

Antisense Prevention of AChE-R Accumulation Promotes Stamina in EAMG Rats

Placed on a treadmill at 25 m/min, healthy rats ran for 23.0±3.0 min, after which time they displayed visible signs of fatigue. Starting at 5 h, and for at least 24 h following administration of 250 µg/Kg rEN101, EAMG rats demonstrated improved performance on the treadmill. Running time increased from 247±35, 179±21 and 32±6 sec to 488±58, 500±193 and 212±59 sec for animals at disease grades 2, 3 and 4, respectively (average values for 6–9 animals per group.) Healthy animals, in contrast, were not significantly affected by rEN101 injection (FIG. 10).

Others have demonstrated efficacy of orally administered 2'-oxymethyl protected AS-ON agents [Monia, B. P. (1997) Ciba Found. Symp. 209, 107–119]. Therefore, the inventors tested this mode in the EAMG model. Based on their own findings, the inventors selected the dose of 50 µg/Kg of rEN101, which was administered to EAMG rats once a day via oral gavage, and CMAP was measured 1, 5, and 24 h later. This dose was as effective as 25 µg/Kg administered i.v. (Table 1 and FIGS. 9 and 13). Orally administered rEN102 was also active in reversing CMAP decline, but its effects appeared somewhat delayed compared to rEN101. Oral pyridostigmine (1000 µg/kg) restored CMAP for up to several hours, while r-invEN102 had no significant effect (Table 1).

EXAMPLE 5

Oral Administration of Human EN101 to EAMG Rats

Human EN101 (hEN101) (0.25 µg/g, single dose) was administered orally to rats with EAMG of medium severity (score 2.5–3.5), which implied the symptoms defined as "moderate" hereunder. The results are summarized in Table 1. Time from treatment is noted above; together with the treadmill running time in sec. Animals were inspected at each time point for evaluation of muscle weakness. The clinical status of the rats was graded according to: (0)—Without definite weakness (treadmill running time, 23±3 min); Mild (1)—weight loss >3% during a week, >10 min. running time on treadmill; Moderate (2)—moderate weakness accompanied by weak grip or cry with fatigue, weight loss of 5–10%, 3–5 min. running on treadmill; Moderate-severe (3)—moderate to severe weakness, hunched back posture at rest, head down and forelimb digit flexed, tremulous ambulation, 10% body weight loss, 1–2 min. run on treadmill); Severe (4)—severe general weakness, no cry or grip, treadmill running time <1 min, weight loss >10%; Death (5). Each line represents an individual rat. It is to be noted that the clinical score (in parentheses) was reduced in all of the treated animals, which reflects time improvement, and that running time was significantly increased for over 5 and 24 hr for most of the animals and for two of the tested animals also at 48 h.

TABLE 2

| | Treadmill Performance Time (Clinical score) | | | |
|---|---|---|---|---|
| Animal | before (basal) | 5 h | 24 h | 48 h | Effect |
| 1 | 110 sec (3) | 150 sec | 360 sec (1) | ND | + + |
| 2 | 0 (3.5) | 70 sec | 30 sec (3) | ND | + − |
| 3 | 210 sec (2.5) | 300 sec | 345 sec (1) | ND | + + |
| 4 | 80 (3) | ND | 170 sec (2) | 85 (2.5) | + − |
| 5 | 180 (2.5) | ||| | 380 (1) | 290 (2) | + + |
| 6 | 30 (3.5) | 120 | |||(3) | ||(5) | + |

These results show that like the rat EN101 (see treadmill example, above), the human EN101 antisense oligodeoxynucleotide of the invention promoted muscle stamina in EAMG induced rats.

EXAMPLE 6

Comparative Analysis of hEN101 and rEN101 in a Rat Animal Model

A study of the potential efficacy as well as toxicity of hEN101 was conducted on 4 week-old Crl:CD rats. To groups of 12 animals (6 males, 6 females) were administered 0.0 (saline only), 0.50 or 2.50 µg/g/day of hEN101 by oral gavage (o.g.), 0.50 µg/g/day of rEN101 by o. g., or 0.50 µg/g/day of rEN101 or hEN101 by i.v. injection. Additionally, there was a control group that was not injected. For 7 days the animals were checked for gross signs of toxicity: mortality, body weight, food consumption, ophtalmology, hematology (peripheral blood), and blood chemistry. At 7 days they were sacrificed and examined post mortem for macroscopic pathology and organ weight. Fixed sections of brain (cerebellum, cerebrum, midbrain, medulla), heart (auricular and ventricular regions), kidneys (cortex, medulla, papilla regions), liver (all main lobes), lungs (two major lobes, including bronchi), lymph nodes (mandibular and mesenteric), spinal cord (transverse and longitudinal sections at cervical, lumbar and thoracic levels), caecum, colon, duodenum, ileum, jejunum, esophagus, rectum, spleen and stomach (keratinized, glandular and antrum) were stained with hematoxylin/eosin to reveal necrosis or cell death.

Mandibular lymph nodes were examined for the effect of EN101 on AChE-R mRNA. Compared to the saline-injected control, rEN101 (oral or i.v.) or hEN101 (i.v.) were inconsistent in depressing AChE-R mRNA levels within these lymph nodes (data not shown). In contrast, the administration of rEN101 (oral or i.v.) or hEN101 (i.v.) did not affect the expression of the AChE-S synaptic variant of AChE in these mandibular lymph nodes (data not shown). Thus, the antisense oligodeoxynucleotide of the invention may be used to suppress the AChE-R variant without affecting the expression of the synaptic variant, i.e. without adversely affecting cholinergic transmission.

EXAMPLE 7

AChE-R Suppression Modifies the Course of EAMG Pathophysiology

As shown in Example 5, unlike anti-cholinesterases, rEN101 afforded long-term maintenance of stable CMAP. This further enabled the inventors to test whether the cholinergic imbalance contributes to the physiological deterioration that is characteristic of EAMG. Rats were first treated with rEN101 once a day for 5 days, CMAPs being determined prior to each treatment. Both the efficacy of rEN101 in retrieving normal CMAP and its capacity to reduce the inter-animal variability in CMAP values reached similar levels to those of pyridostigmine (FIGS. 11A and 11B). However, the onset of response to pyridostigmine was more rapid (Table 1), while that observed with rEN101 was longer-lasting. Daily oral or i.v administration of rEN101 stabilized CMAPs over the entire course of treatment (FIG. 11B). In contrast, the effect of pyridostigmine wore off within several hours, causing pronounced fluctuations in muscle status (Table 1 and FIG. 11). Among the animals treated daily with pyridostigmine, 5 out of 6 died within the 5 day experimental course. In contrast, 6 out of 8 animals treated once-a-day with rEN101 via o.g. survived the full 5 day period. This conspicuous difference might reflect the susceptibility of EAMG rats to repeated anesthesia and CMAP measurements. In order to avoid these additional stresses and evaluate the effect of the antisense treatment on EAMG pathophysiology, the inventors subjected groups of moderately sick animals to 1 month of daily oral treatment with minimal interference. EAMG rats receiving oral doses of rEN101 daily, presented significant improvement in survival, clinical status and treadmill performance, as compared with pyridostigmine- and saline-treated animals (FIG. 12; $P<0.041$ for 4 weeks survival incidence, Fisher exact test, AS-ON vs. other treatments). One way repeated measures ANOVA yielded $P<0.05$ for all other measures (AS vs. other treatments at 4 weeks). The effect of rEN101 on clinical symptoms was also corroborated by body weight changes. Rats treated with saline and Mestinon treated groups lost 13.5 and 11 g/animal, respectively, whereas animals treated with rEN101 gained, on average, 13 g during the treatment period. Thus, daily rEN101 administration promoted long-term change in the course of EAMG in rats with moderate to severe symptoms, under the same conditions in which untreated or pyridostigmine-treated animals deteriorated.

By using MG and EAMG as case studies for evaluating the consequences of chronic neuromuscular imbalance at the level of gene expression, the inventors confirmed that the AChE-R variant is systemically elevated in MG and EAMG. Moreover, the inventors showed that antisense suppression of AChE-R normalized NMJ responses to repeated nerve stimulation, promoting muscle strength, and recuperating a healthier status in animals otherwise too weak even to eat. These observations support the idea that AChE-R plays a direct role in MG pathophysiology and call for evaluation of the rationale of long-term mRNA-targeted therapy for imbalanced cholinergic function at NMJs.

EXAMPLE 8

Oral Administration of hEN101 to Cynomolgus Monkeys

This experiment was conducted with six (3 males and 3 females) purpose-bred 15 month-old (young adult) Cynomolgus monkeys, divided in three groups (1, 2 and 3) of one male and one female each. Groups 1 and 2 received hEN101 daily by o.g. for a period of 7 days, at a concentration of 0.15 and 0.50 μg/g/day, respectively. Group 3 received daily i.v. injections of hEN101 for a period of 7 days at a dosage of 0.50 μg/g/day.

Over a 12 hour period, plasma samples were obtained during the second treatment day to investigate the toxicokinetic profile at each dosage. The toxicology study consisted of checking the animals during the 7 days of treatment for gross signs of toxicity by the following parameters: mortality, body weight, food consumption, electrocardiography, blood pressure, hematology (peripheral blood), and blood chemistry. At 7 days the monkeys were sacrificed and examined post-mortem for macroscopic pathology and organ weight. Fixed sections of brain (cerebellum, cerebrum, midbrain, medulla), caecum, colon, duodenum, heart (auricular and ventriclar regions), ileum, jejunum, kidneys (cortex, medulla, papilla regions), liver (two main lobes), lungs (two major lobes, including bronchi), lymph nodes (mandibular and mesenteric), esophagus, rectum, sciatic nerve, skeletal muscle (thigh), spinal cord (transverse and longitudinal sections at cervical level), spleen and stomach (body and antrum) were stained with hematoxylin/eosin to reveal necrosis or cell death.

These clinical investigations revealed no toxicological effects by any of the treatment protocols. Post-mortem there were no treatment-related effects other than slight healing erosions in the body of the stomach, which are possibly associated with treatment, in 1 of 2 animals in each group, and some irritation of the perivascular tissue at the site of intravenous injection.

Paraffin-embedded 7 μm spinal cord sections were examined by in situ hybridization for the levels of AChE-R and AChE-S mRNA. Under all three regimens (oral 0.15 and 0.50, and i.v. 0.50 μg/g/day), there was no apparent reduction in AChE-S mRNA (FIG. 14). However, there was a significant reduction in AChE-R mRNA in increasing hEN101 daily dose from 0.15 (oral) to 0.50 (oral or i.v.) with i.v. dosage being more effective.

AChE-R-positive sections from monkey spinal cords were analyzed for the relation between cell body diameter and percentage of AChE-R positive cells (FIG. 15). Cells were divided into three categories according to their body diameter, and the percentage of AChE-R-positive cells from each category was evaluated. Treatment with the lower concentration of EN101 (150 μg/kg/day) caused an increase in the percent of small AChE-R-positive cells (<70 μm diameter) as compared to naive monkeys, probably due to the injection stress response, which is known to raise AChE-R mRNA levels (Kaufer et al, 1998). Either i.v. or p.o. administration of the higher EN101 concentration (500 μg/kg/day) reduced the percentage of AChE-R-positive neurons, compared to the lower concentration ($p<0.05$, Student's t test). The decrease was more remarkable in small neurons (23–40 μm) than in neurons with cell body diameter of 40–70 μm, and no decrease was observed in large neurons (>70 μm diameter) (FIG. 15). The percentage of small- (23 to 40 μm-diameter) and medium-sized (40 to 70 μm) neurons that were labeled decreased significantly in moving from the lower to the higher hEN 101 oral dose, and even further with the i.v. administration. Among the larger neurons (>70 μm), there was not discernable effect of hEN101. We have yet to discover the functional correlate of cell size that determines the efficacy of antisense suppression of AChE-R expression. This suggests that EN101 will prevent the stress-induced impairment in interneurons input to motoneurons, thus preventing paralysis—e.g. post-surgery.

EXAMPLE 9 hEN101 Suppression of AChE Activity in Monkey Plasma

In the 12 hr following the second day administration of hEN101, monkey plasma samples were collected and stored. Plasma cholinesterase activities were measured by spectrophotometry assessing the rate of hydrolysis of acetylthiocholine (measured by the Ellman assay, which quantifies the hydrolysis of acetylthiocholine) [Ellman, G. L., et al. (1961), Biochem. Pharmacol. 7, 88–95], in the absence or presence of iso-OMPA (a selective butyrylcholinesterase, BChE, inhibitor). Total activity, largely due to serum BChE, was generally unchanged (FIG. 16A). When measured in the presence of $1 \times 10^{-5}$M iso-OMPA, AChE activity increased within the 5 hr post-injection. This increase, observed under 150 μg/kg was effectively suppressed or attenuated by the higher dose of 500 μg/kg hEN101, and even more effective when this dose was i.v. administered (FIG. 16B).

EXAMPLE 10

Effect of rEN101 on Expression AChE-R mRNA in Rat Spinal Cord Neurons

Contrary to the effect of hEN101 on monkey spinal cord neurons, rEN101 does not suppress AChE-R mRNA in the rat spinal cord (FIG. 17), when assessed by in situ hybridization using a mouse probe. Neither the number of positive cells nor the staining intensity were significantly changed. One explanation for this result would be that the blood-brain barrier that isolates the CNS is more permeable in monkeys than rats, at least under the chosen experimental conditions.

EXAMPLE 11 hEN101 Phase Ib Clinical Trial 16 patients with stable generalized MG requiring constant AChE inhibitors (pyridostigmine) for daily function were recruited, after approval by human ethics committees of the respective hospitals involved in the present trial (Hadassah Medical Center, Jerusalem, Israel and Greater Manchester Neurosciences Center, Hope Hospital, Salford, England).

Analysis of the results obtained from the Clinical trial showed that in 15 out of 16 patients, the initial deterioration in MG status after stopping pyridostigmine was followed by a clear symptomatic improvement due to hEN101. As an example, FIG. 18 shows the improvement in ptosis in one of the MG patients. Analysis of the mean daily QMG scores showed a continuous decrease in each of the study days (decrease in QMG means improvement in disease status) (FIGS. 21A and 21B). The baseline (entry) mean total score was 13.2. The score decreased for days 2 through 6 in the amounts of 3.0, 4.8, 5.7, 5.5 and 6.0 ($p<0.001$). The mean percent improvement of total QMG for these days ranged from 27.8% to 53.4% (FIG. 20) ($p<0.01$). All individual test item scores, except for vital capacity and left arm out stretched time, had statistically significant change from entry for days 2–6 ($p<0.05$). Improved QCG scores following the final dose of hEN101 were sustained for up to 72 hours. No serious adverse effects were observed. Vital signs, chemical chemistry, hematology, urinalysis, ECG and physical examination remained unchanged throughout the experimental period and in the month following discharge. Cholinergic side effects were not reported.

Thus, hEN101 appears to be powerfully effective in reversing symptoms in patients with stable MG. The present study showed that hEN101 has potential advantages over conventional cholinesterase inhibitors with respect to dosing, specificity, side-effect profile, duration of efficacy and treatment regimen.

---

The invention claimed is:

1. A synthetic antisense oligodeoxynucleotide targeted against human AChE mRNA, which synthetic antisense oligodeoxynucleotide comprises the nucleotide sequence:
5' CTGCCACGTTCTCCTGCACC 3' (SEQ ID NO:1).

2. A synthetic nuclease resistant antisense oligodeoxynucleotide, the nucleotide sequence of which is:
5' CTGCCACGTTCTCCTGCACC 3' (SEQ ID NO:1).

3. The synthetic antisense oligodeoxynucleotide of claim 2, which is a modified oligodeoxynucleotide comprising a partially unsaturated aliphatic hydrocarbon chain and which oligonucleotid comprises at least one polar or charged group selected from the group consisting of a carboxylic acid group, an ester group, and an alcohol group.

4. The synthetic nuclease resistant antisense oligodeoxynucleotide of claim 2 or 3, wherein at least one of the three last nucleotides from the 3'-terminus is 2'-O-methylated.

5. The synthetic nuclease resistant antisense oligodeoxynucleotide of claim 4, in which the three last nucleotides are 2'-O-methylated.

6. The synthetic nuclease resistant antisense oligodeoxynucleotide of claim 2, wherein at least one nucleotide is fluoridated.

7. The synthetic nuclease resistant antisense oligodeoxynucleotide of claim 2 or claim 3, having phosphorothioate bonds linking at least the two last nucleotide bases from the 3'-terminus.

8. The synthetic nuclease resistant antisense oligodeoxynucleotide of claim 7, having phosphorothioate bonds linking the last four nucleotide bases from the 3'-terminus.

9. The synthetic nuclease resistant antisense oligodeoxynucleotide of claim 3, further comprising a sequence of nucleotides at the 3'-end region, wherein said sequence of nucleotides at the 3' end region forms a loop structure.

10. The synthetic nuclease resistant antisense oligodeoxynucleotide of claim 9, wherein said loop structure is a 9-nucleotide loop, the sequence of which is CGCGAAGCG (SEQ ID NO:2).

11. A pharmaceutical composition comprising the antisense oligonucleotide hEN101 defined by SEQ ID NO: 1, as active ingredient, and further comprising a pharmaceutically acceptable adjuvant, carrier or diluent.

12. The pharmaceutical composition of claim 11, which is for daily use by a patient and which comprises a dosage of active ingredient between 0.001 µg/g and 50 µg/g.

13. The pharmaceutical composition of claim 11, further comprising at least one additional active agent.

14. A method of preparation of a pharmaceutical composition comprising the step of admixing the antisense oligonucleotide hEN101, defined by SEQ ID NO:1, with a pharmaceutically acceptable adjuvant, carrier or diluent, and optionally with at least one additional active agent.

* * * * *

SEQUENCE LISTING

```
<160> NUMBER OF SEQ ID NOS: 6
<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: human
      EN101

<400> SEQUENCE: 1
ctgccacgtt ctcctgcacc                                               20

<210> SEQ ID NO 2
<211> LENGTH: 9
<212> TYPE: DNA
<213> ORGANISM: Artificial Sequence
<220> FEATURE:
<223> OTHER INFORMATION: Description of Artificial Sequence: loop within
      hEN101

<400> SEQUENCE: 2 cgcgaagcg                                                            9

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:mouse EN101

<400> SEQUENCE: 3
ctgcaatatt ttcttgcacc                                               20

<210> SEQ ID NO 4
<211> LENGTH: 20
```

-continued

```
<212> TYPE: DNA
<213> ORGANISM: Artificial Sequence
<220> FEATURE:
<223> OTHER INFORMATION: Description of Artificial Sequence:rat EN101

<400> SEQUENCE: 4
ctgcgatatt ttcttgtacc                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: rat EN102

<400> SEQUENCE: 5
gggagaggag gaggaagagg                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:rat invEN102

<400> SEQUENCE: 6
ggagaaggag gaggagaggg                                              20
```